United States Patent [19]
Kishimoto et al.

[11] Patent Number: 5,719,042
[45] Date of Patent: Feb. 17, 1998

[54] NUCLEIC ACIDS ENCODING TRANSCRIPTION FACTOR APRF (ACUTE PHASE RESPONSE FACTOR)

[75] Inventors: Tadamitsu Kishimoto, 3-5-31, Nakanocho, Tondabayashi-shi, Osaka; Shizuo Akira, Osaka, both of Japan

[73] Assignee: Tadamitsu Kishimoto, Osaka, Japan

[21] Appl. No.: 416,581

[22] Filed: Apr. 4, 1995

[30] Foreign Application Priority Data

Apr. 4, 1994 [JP] Japan .................... 6-065825

[51] Int. Cl.$^6$ .................... C12P 21/06; C12N 15/63; C12N 5/00; C07H 21/04
[52] U.S. Cl. .................... 435/69.1; 435/252.33; 435/320.1; 435/356; 435/358; 435/365; 536/23.5
[58] Field of Search .................... 435/69.1, 240.1, 435/240.2, 252.3, 252.33, 254.2, 320.1, 356, 358, 365; 536/23.1, 23.5

[56] References Cited

PUBLICATIONS

*Trying on a New Pair of SH2s*, Marc Montminy, Science, vol. 261, pp. 1694–1695, Sep. 1993.
*A nuclear factor for IL–6* . . . , S. Akira et al., The EMBO Journal, vol. 9, No. 6, pp. 1897–1906, 1990.
*IL–6DBP, a Nuclear Protein* . . . , Valeria Poli et al, Cell, vol. 63, pp. 643–653, Nov. 1990.
*A member of the C/EBP family* . . . , Shigemi Kinoshita et al, Proc. Natl. Acad. vol. 89 pp. 1473–1476, Feb. 1992.
*Acute–Phase Response Factor*, Ursula M. Wegenka et al, Molecular 7 Cellular Bio., pp. 276–288, Jan. 1993.
*Molecular Cloning of APRF* . . . , S. Akira et al, Cell, vol. 77, pp. 63–71, Apr. 1994.

Maniatis et al. Hybridization to nitrocellulose filters containing replicas of bacteriophage plaques or bacterial colonies in Molecular Cloning: A Laboratory Manual. Cold Spring Harbor Laboratory, Cold Spring Harbor, New York, pp. 326–328, 1982.

Zhong et al. Stat3: A STAT family member activated by tyrosine phosphorylation in response to epidermal growth factor and Interleukin–6. Science 264:95–98, 1994.

Wegenka et al. The Interleukin–6–activated acute–phase–response–factor is antigenically and functionally related to members of the signal transducer and activator of transcription (STAT) family. Molecular and Cellular Biology. 14(5):3186–3196, 1994.

Zhong et al. Stat3 and Stat4: Members of the family of signal transducers and activators of transcription. PNAS USA. 91(11):4806–4810, 1994.

*Primary Examiner*—Douglas W. Robinson
*Assistant Examiner*—Thanda Wai
*Attorney, Agent, or Firm*—Sughrue, Mion, Zinn, Macpeak & Seas, PLLC

[57] ABSTRACT

Mammal transcription factor APRF, process for the preparation of it, DNAs encoding the product, replication and expression vector comprising the DNA, host cells transformed or tranfected with the replication and expression vector, evaluating and screening method for searching an inhibitory agent on the function of APRF and an inhibitory agent against the function of the APRF. The peptide of the present invention (APRF) may be useful for complement or suppression of the function of APRF, screening an inhibitory agent against the function of APRF. Inhibiting agent containing the product as active ingredient of the present invention may be also useful for treatment of diseases related to cytokine such as IL–6, i.e., inflammatory diseases.

8 Claims, No Drawings

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 770 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:1:

```
Met Ala Gln Trp Asn Gln Leu Gln Gln Leu Asp Thr Arg Tyr Leu Glu
1               5                   10                  15
Gln Leu His Gln Leu Tyr Ser Asp Ser Phe Pro Met Glu Leu Arg Gln
            20                  25                  30
Phe Leu Ala Pro Trp Ile Glu Ser Gln Asp Trp Ala Tyr Ala Ala Ser
            35                  40                  45
Lys Glu Ser His Ala Thr Leu Val Phe His Asn Leu Leu Gly Glu Ile
    50                  55                  60
Asp Gln Gln Tyr Ser Arg Phe Leu Gln Glu Ser Asn Val Leu Tyr Gln
65                  70                  75                  80
His Asn Leu Arg Arg Ile Lys Gln Phe Leu Gln Ser Arg Tyr Leu Glu
                85                  90                  95
Lys Pro Met Glu Ile Ala Arg Ile Val Ala Arg Cys Leu Trp Glu Glu
            100                 105                 110
Ser Arg Leu Leu Gln Thr Ala Ala Thr Ala Ala Gln Gln Gly Gly Gln
            115                 120                 125
Ala Asn His Pro Thr Ala Ala Val Val Thr Glu Lys Gln Gln Met Leu
    130                 135                 140
Glu Gln His Leu Gln Asp Val Arg Lys Arg Val Gln Asp Leu Glu Gln
145                 150                 155                 160
Lys Met Lys Val Val Glu Asn Leu Gln Asp Asp Phe Asp Phe Asn Tyr
                165                 170                 175
Lys Thr Leu Lys Ser Gln Gly Asp Met Gln Asp Leu Asn Gly Asn Asn
            180                 185                 190
Gln Ser Val Thr Arg Gln Lys Met Gln Gln Leu Glu Gln Met Leu Thr
            195                 200                 205
Ala Leu Asp Gln Met Arg Arg Ser Ile Val Ser Glu Leu Ala Gly Leu
    210                 215                 220
Leu Ser Ala Met Glu Tyr Val Gln Lys Thr Leu Thr Asp Glu Glu Leu
225                 230                 235                 240
Ala Asp Trp Lys Arg Arg Gln Gln Ile Ala Cys Ile Gly Gly Pro Pro
                245                 250                 255
Asn Ile Cys Leu Asp Arg Leu Glu Asn Trp Ile Thr Ser Leu Ala Glu
            260                 265                 270
Ser Gln Leu Gln Thr Arg Gln Gln Ile Lys Lys Leu Glu Glu Leu His
    275                 280                 285
Gln Lys Val Ser Tyr Lys Gly Asp Pro Ile Val Gln His Arg Pro Met
290                 295                 300
Leu Glu Glu Arg Ile Val Glu Leu Phe Arg Asn Leu Met Lys Ser Ala
305                 310                 315                 320
Phe Val Val Glu Arg Gln Pro Cys Met Pro Met His Pro Asp Arg Pro
                325                 330                 335
Leu Val Ile Lys Thr Gly Val Gln Phe Thr Thr Lys Val Arg Leu Leu
            340                 345                 350
Val Lys Phe Pro Glu Leu Asn Tyr Gln Leu Lys Ile Lys Val Cys Ile
        355                 360                 365
Asp Lys Asp Ser Gly Asp Val Ala Ala Leu Arg Gly Ser Arg Lys Phe
    370                 375                 380
Asn Ile Leu Gly Thr Asn Thr Lys Val Met Asn Met Glu Glu Ser Asn
385                 390                 395                 400
Asn Gly Ser Leu Ser Ala Glu Phe Lys His Leu Thr Leu Arg Glu Gln
                405                 410                 415
Arg Cys Gly Asn Gly Gly Arg Ala Asn Cys Asp Ala Ser Leu Ile Val
```

-continued

```
                        420                         425                         430
    Thr  Glu  Glu  Leu  His  Leu  Ile  Thr  Phe  Glu  Thr  Glu  Val  Tyr  His  Gln
              435                         440                         445
    Gly  Leu  Lys  Ile  Asp  Leu  Glu  Thr  His  Ser  Leu  Ser  Val  Val  Val  Ile
         450                         455                         460
    Ser  Asn  Ile  Cys  Gln  Met  Pro  Asn  Ala  Trp  Ala  Ser  Ile  Leu  Trp  Tyr
    465                         470                         475                    480
    Asn  Met  Leu  Thr  Asn  Asn  Pro  Lys  Asn  Val  Asn  Phe  Phe  Thr  Lys  Pro
                        485                         490                         495
    Pro  Ile  Gly  Thr  Trp  Asp  Gln  Val  Ala  Glu  Val  Leu  Ser  Trp  Gln  Phe
                   500                         505                         510
    Ser  Ser  Thr  Thr  Lys  Arg  Gly  Leu  Ser  Ile  Glu  Gln  Leu  Thr  Thr  Leu
              515                         520                         525
    Ala  Glu  Lys  Leu  Leu  Gly  Pro  Gly  Val  Asn  Tyr  Ser  Gly  Cys  Gln  Ile
         530                         535                         540
    Thr  Trp  Ala  Asn  Phe  Cys  Lys  Glu  Asn  Met  Ala  Gly  Lys  Gly  Phe  Ser
    545                         550                         555                    560
    Tyr  Trp  Val  Trp  Leu  Asp  Asn  Ile  Ile  Asp  Leu  Val  Lys  Lys  Tyr  Ile
                   565                         570                         575
    Leu  Ala  Leu  Trp  Asn  Glu  Gly  Tyr  Ile  Met  Gly  Phe  Ile  Ser  Lys  Glu
                   580                         585                         590
    Arg  Glu  Arg  Ala  Ile  Leu  Ser  Thr  Lys  Pro  Pro  Gly  Thr  Phe  Leu  Leu
              595                         600                         605
    Arg  Phe  Ser  Glu  Ser  Ser  Lys  Glu  Gly  Gly  Val  Thr  Phe  Thr  Trp  Val
         610                         615                         620
    Glu  Lys  Asp  Ile  Ser  Gly  Lys  Thr  Gln  Ile  Gln  Ser  Val  Glu  Pro  Tyr
    625                         630                         635                    640
    Thr  Lys  Gln  Gln  Leu  Asn  Asn  Met  Ser  Phe  Ala  Glu  Ile  Ile  Met  Gly
                        645                         650                         655
    Tyr  Lys  Ile  Met  Asp  Ala  Thr  Asn  Ile  Leu  Leu  Ser  Pro  Leu  Val  Tyr
                   660                         665                         670
    Leu  Tyr  Pro  Asp  Ile  Pro  Lys  Glu  Glu  Ala  Phe  Gly  Lys  Tyr  Cys  Arg
              675                         680                         685
    Pro  Glu  Ser  Gln  Glu  His  Pro  Glu  Ala  Asp  Pro  Gly  Ser  Ala  Ala  Pro
         690                         695                         700
    Tyr  Leu  Lys  Thr  Lys  Phe  Ile  Cys  Val  Thr  Pro  Thr  Thr  Cys  Ser  Asn
    705                         710                         715                    720
    Thr  Ile  Asp  Leu  Pro  Met  Ser  Pro  Arg  Ala  Leu  Asp  Ser  Leu  Met  Gln
                        725                         730                         735
    Phe  Gly  Asn  Asn  Gly  Glu  Gly  Ala  Glu  Pro  Ser  Ala  Gly  Gly  Gln  Phe
                   740                         745                         750
    Glu  Ser  Leu  Thr  Phe  Asp  Met  Glu  Leu  Thr  Ser  Glu  Cys  Ala  Thr  Ser
              755                         760                         765
    Pro  Met
    770
```

( 2 ) INFORMATION FOR SEQ ID NO:2:

( i ) SEQUENCE CHARACTERISTICS:
        ( A ) LENGTH: 2310 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:2:

```
ATGGCCCAAT GGAATCAGCT ACAGCAGCTT GACACACGGT ACCTGGAGCA GCTCCATCAG      60
CTCTACAGTG ACAGCTTCCC AATGGAGCTG CGGCAGTTTC TGGCCCCTTG GATTGAGAGT     120
CAAGATTGGG CATATGCGGC CAGCAAAGAA TCACATGCCA CTTTGGTGTT TCATAATCTC     180
CTGGGAGAGA TTGACCAGCA GTATAGCCGC TTCCTGCAAG AGTCGAATGT TCTCTATCAG     240
CACAATCTAC GAAGAATCAA GCAGTTTCTT CAGAGCAGGT ATCTTGAGAA GCCAATGGAG     300
ATTGCCCGGA TTGTGGCCCG GTGCCTGTGG GAAGAATCAC GCCTTCTACA GACTGCAGCC     360
ACTGCGGCCC AGCAAGGGGG CCAGGCCAAC CACCCCACAG CAGCCGTGGT GACGGAGAAG     420
CAGCAGATGC TGGAGCAGCA CCTTCAGGAT GTCCGGAAGA GAGTGCAGGA TCTAGAACAG     480
AAAATGAAAG TGGTAGAGAA TCTCCAGGAT GACTTTGATT TCAACTATAA AACCCTCAAG     540
AGTCAAGGAG ACATGCAAGA TCTGAATGGA ACAACCAGT CAGTGACCAG GCAGAAGATG     600
CAGCAGCTGG AACAGATGCT CACTGCGCTG GACCAGATGC GGAGAAGCAT CGTGAGTGAG     660
CTGGCGGGGC TTTTGTCAGC GATGGAGTAC GTGCAGAAAA CTCTCACGGA CGAGGAGCTG     720
GCTGACTGGA AGAGGCGGCA ACAGATTGCC TGCATTGGAG GCCCGCCCAA CATCTGCCTA     780
GATCGGCTAG AAAACTGGAT AACGTCATTA GCAGAATCTC AACTTCAGAC CCGTCAACAA     840
ATTAAGAAAC TGGAGGAGTT GCACCAAAAA GTTCCTACA AAGGGGACCC CATTGTACAG     900
CACCGGCCGA TGCTGGAGGA GAGGATCGTG GAGCTGTTCA GAAACTTAAT GAAAAGTGCC     960
TTTGTGGTGG AGCGGCAGCC CTGCATGCCC ATGCATCCTG ACCGGCCCCT CGTCATCAAG    1020
ACCGGCGTCC AGTTCACTAC TAAAGTCAGG TTGCTGGTCA AGTTCCCTGA GTTGAATTAT    1080
CAGCTTAAAA TTAAAGTGTG CATTGACAAA GACTCTGGGG ACGTTGCAGC TCTCAGAGGA    1140
TCCCGGAAAT TTAACATTCT GGGCACAAAC ACAAAAGTGA TGAACATGGA AGAATCCAAC    1200
AACGGCAGCC TCTCTGCAGA ATTCAAACAC TTGACCCTGA GGGAGCAGAG ATGTGGGAAT    1260
GGGGGCCGAG CCAATTGTGA TGCTTCCCTG ATTGTGACTG AGGAGCTGCA CCTGATCACC    1320
TTTGAGACCG AGGTGTATCA CCAAGGTCTC AAGATTGACC TAGAGACCCA CTCCTTGTCA    1380
GTTGTGGTGA TCTCCAACAT CTGTCAGATG CCAAATGCCT GGGCGTCCAT CCTGTGGTAC    1440
AACATGCTGA CCAACAATCC CAAGAATGTG AACTTCTTCA CTAAGCCGCC AATTGGAACC    1500
TGGGACCAAG TGGCCGAGGT GCTCAGCTGG CAGTTCTCGT CCACCACCAA GCGGGGGCTG    1560
AGCATCGAGC AGCTGACAAC GCTGGCTGAG AAGCTCCTAG GCCTGGTGT GAACTACTCA    1620
GGGTGTCAGA TCACATGGGC TAACTTCTGC AAAGAAAACA TGGCTGGCAA GGGCTTCTCC    1680
TACTGGGTCT GGCTAGACAA TATCATCGAC CTTGTGAAAA AGTATATCTT GGCCCTTTGG    1740
AATGAAGGGT ACATCATGGG TTTCATCAGC AAGGAGCGGG AGCGGGCCAT CTTGAGCACT    1800
AAGCCCCCAG GCACCTTCCT GCTGCGCTTC AGTGAAAGCA GCAAGGAAGG AGGCGTCACT    1860
TTCACTTGGG TGGAGAAGGA CATCAGCGGT AAGACCCAGA TCCAGTCCGT GGAACCATAC    1920
ACAAAGCAGC AGCTGAACAA CATGTCATTT GCTGAAATCA TCATGGGCTA TAAGATCATG    1980
GATGCTACCA ATATCCTGTT GTCTCCACTT GTCTATCTCT ATCCTGACAT TCCCAAGGAG    2040
GAGGCATTCG GGAAGTATTG TCGGCCAGAG AGCCAGGAGC ATCCTGAAGC TGACCCAGGT    2100
AGCGCTGCCC CATACCTGAA GACCAAGTTT ATCTGTGTGA CACCAACGAC CTGCAGCAAT    2160
ACCATTGACC TGCCGATGTC CCCCCGCGCT TTAGATTCAT TGATGCAGTT TGGAAATAAT    2220
GGTGAAGGTG CTGAACCCTC AGCAGGAGGG CAGTTTGAGT CCCTCACCTT TGACATGGAG    2280
TTGACCTCGG AGTGCGCTAC CTCCCCCATG                                     2310
```

( 2 ) INFORMATION FOR SEQ ID NO:3:

( i ) SEQUENCE CHARACTERISTICS:
        ( A ) LENGTH: 2787 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:3:

```
CAGCTGGAAT  TCGGGGCGGC  GGCGCAGACT  GGGAGGGGGA  GCCGGGGGTT  CCGACGTCGC    60
AGCCGAGGGA  ACAAGCCCCA  ACCGGATCCT  GGACAGGCAC  CCCGGCTTGG  CGCTGTCTCT   120
CCCCCTCGGC  TCGGAGAGGC  CCTTCGGCCT  GAGGGAGCCT  CGCCGCCCGT  CCCCGGCACA   180
CGCGCAGCCC  CGGCCTCTCG  GCCTCTGCCG  GAGAAACAGG  ATGGCCCAAT  GGAATCAGCT   240
ACAGCAGCTT  GACACACGGT  ACCTGGAGCA  GCTCCATCAG  CTCTACAGTG  ACAGCTTCCC   300
AATGGAGCTG  CGGCAGTTTC  TGGCCCCTTG  GATTGAGAGT  CAAGATTGGG  CATATGCGGC   360
CAGCAAAGAA  TCACATGCCA  CTTTGGTGTT  TCATAATCTC  CTGGGAGAGA  TTGACCAGCA   420
GTATAGCCGC  TTCCTGCAAG  AGTCGAATGT  TCTCTATCAG  CACAATCTAC  GAAGAATCAA   480
GCAGTTTCTT  CAGAGCAGGT  ATCTTGAGAA  GCCAATGGAG  ATTGCCCGGA  TTGTGGCCCG   540
GTGCCTGTGG  GAAGAATCAC  GCCTTCTACA  GACTGCAGCC  ACTGCGGCCC  AGCAAGGGGG   600
CCAGGCCAAC  CACCCCACAG  CAGCCGTGGT  GACGGAGAAG  CAGCAGATGC  TGGAGCAGCA   660
CCTTCAGGAT  GTCCGGAAGA  GAGTGCAGGA  TCTAGAACAG  AAAATGAAAG  TGGTAGAGAA   720
TCTCCAGGAT  GACTTTGATT  TCAACTATAA  AACCCTCAAG  AGTCAAGGAG  ACATGCAAGA   780
TCTGAATGGA  AACAACCAGT  CAGTGACCAG  GCAGAAGATG  CAGCAGCTGG  AACAGATGCT   840
CACTGCGCTG  GACCAGATGC  GGAGAAGCAT  CGTGAGTGAG  CTGGCGGGGC  TTTTGTCAGC   900
GATGGAGTAC  GTGCAGAAAA  CTCTCACGGA  CGAGGAGCTG  GCTGACTGGA  AGAGGCGGCA   960
ACAGATTGCC  TGCATTGGAG  GCCCGCCCAA  CATCTGCCTA  GATCGGCTAG  AAAACTGGAT  1020
AACGTCATTA  GCAGAATCTC  AACTTCAGAC  CCGTCAACAA  ATTAAGAAAC  TGGAGGAGTT  1080
GCACCAAAAA  GTTTCCTACA  AAGGGGACCC  CATTGTACAG  CACCGGCCGA  TGCTGGAGGA  1140
GAGGATCGTG  GAGCTGTTCA  GAAACTTAAT  GAAAAGTGCC  TTTGTGGTGG  AGCGGCAGCC  1200
CTGCATGCCC  ATGCATCCTG  ACCGGCCCCT  CGTCATCAAG  ACCGGCGTCC  AGTTCACTAC  1260
TAAAGTCAGG  TTGCTGGTCA  AGTTCCCTGA  GTTGAATTAT  CAGCTTAAAA  TTAAAGTGTG  1320
CATTGACAAA  GACTCTGGGG  ACGTTGCAGC  TCTCAGAGGA  TCCCGGAAAT  TTAACATTCT  1380
GGGCACAAAC  ACAAAAGTGA  TGAACATGGA  AGAATCCAAC  AACGGCAGCC  TCTCTGCAGA  1440
ATTCAAACAC  TTGACCCTGA  GGGAGCAGAG  ATGTGGGAAT  GGGGCCGAG   CCAATTGTGA  1500
TGCTTCCCTG  ATTGTGACTG  AGGAGCTGCA  CCTGATCACC  TTTGAGACCG  AGGTGTATCA  1560
CCAAGGTCTC  AAGATTGACC  TAGAGACCCA  CTCCTTGTCA  GTTGTGGTGA  TCTCCAACAT  1620
CTGTCAGATG  CCAAATGCCT  GGGCGTCCAT  CCTGTGGTAC  AACATGCTGA  CCAACAATCC  1680
CAAGAATGTG  AACTTCTTCA  CTAAGCCGCC  AATTGGAACC  TGGGACCAAG  TGGCCGAGGT  1740
GCTCAGCTGG  CAGTTCTCGT  CCACCACCAA  GCGGGGGCTG  AGCATCGAGC  AGCTGACAAC  1800
GCTGGCTGAG  AAGCTCCTAG  GGCCTGGTGT  GAACTACTCA  GGGTGTCAGA  TCACATGGGC  1860
TAACTTCTGC  AAAGAAAACA  TGGCTGGCAA  GGGCTTCTCC  TACTGGGTCT  GGCTAGACAA  1920
TATCATCGAC  CTTGTGAAAA  AGTATATCTT  GGCCCTTTGG  AATGAAGGGT  ACATCATGGG  1980
TTTCATCAGC  AAGGAGCGGG  AGCGGGCCAT  CTTGAGCACT  AAGCCCCCAG  GCACCTTCCT  2040
```

| | | | | | |
|---|---|---|---|---|---|
| GCTGCGCTTC | AGTGAAAGCA | GCAAAGAAGG | AGGCGTCACT | TTCACTTGGG | TGGAGAAGGA | 2100 |
| CATCAGCGGT | AAGACCCAGA | TCCAGTCCGT | GGAACCATAC | ACAAAGCAGC | AGCTGAACAA | 2160 |
| CATGTCATTT | GCTGAAATCA | TCATGGGCTA | TAAGATCATG | GATGCTACCA | ATATCCTGTT | 2220 |
| GTCTCCACTT | GTCTATCTCT | ATCCTGACAT | TCCCAAGGAG | GAGGCATTCG | GGAAGTATTG | 2280 |
| TCGGCCAGAG | AGCCAGGAGC | ATCCTGAAGC | TGACCCAGGT | AGCGCTGCCC | CATACCTGAA | 2340 |
| GACCAAGTTT | ATCTGTGTGA | CACCAACGAC | CTGCAGCAAT | ACCATTGACC | TGCCGATGTC | 2400 |
| CCCCCGCGCT | TTAGATTCAT | TGATGCAGTT | TGGAAATAAT | GGTGAAGGTG | CTGAACCCTC | 2460 |
| AGCAGGAGGG | CAGTTTGAGT | CCCTCACCTT | TGACATGGAG | TTGACCTCGG | AGTGCGCTAC | 2520 |
| CTCCCCCATG | TGAGGAGCTG | AGAACGGAAG | CTGCAGAAAG | ATACGACTGA | GGCGCCTACC | 2580 |
| TGCATTCTGC | CACCCCTCAC | ACAGCAAAC | CCCAGATCAT | CTGAAACTAC | TAACTTTGTG | 2640 |
| GTTCCAGATT | TTTTTAATC | TCCTACTTCT | GCTATCTTTG | AGCAATCTGG | GCACTTTTAA | 2700 |
| AAATAGAGAA | ATGAGTGAAT | GTGGGTGATC | TGCTTTTATC | TAAATGCAAA | TAAGGATGTG | 2760 |
| TTCTCTGAGA | CCCATGATCA | GGGGATG | | | | 2787 |

( 2 ) INFORMATION FOR SEQ ID NO:4:

( i ) SEQUENCE CHARACTERISTICS:
        ( A ) LENGTH: 2787 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Homo sapiens
        ( F ) TISSUE TYPE: Placenta ( i x ) FEATURE:
        ( A ) NAME/KEY: CDS
        ( B ) LOCATION: 221..2530

( x i ) SEQUENCE DESCRIPTION: SEQ ID NO:4:

```
CAGCTGGAAT TCGGGGCGGC GGCGCAGACT GGGAGGGGGA GCCGGGGGTT CCGACGTCGC        60

AGCCGAGGGA ACAAGCCCCA ACCGGATCCT GGACAGGCAC CCCGGCTTGG CGCTGTCTCT       120

CCCCCTCGGC TCGGAGAGGC CCTTCGGCCT GAGGGAGCCT CGCCGCCCGT CCCCGGCACA       180

CGCGCAGCCC CGGCCTCTCG GCCTCTGCCG GAGAAACAGG ATG GCC CAA TGG AAT        235
                                              Met Ala Gln Trp Asn
                                                1               5

CAG CTA CAG CAG CTT GAC ACA CGG TAC CTG GAG CAG CTC CAT CAG CTC        283
Gln Leu Gln Gln Leu Asp Thr Arg Tyr Leu Glu Gln Leu His Gln Leu
         10                  15                  20

TAC AGT GAC AGC TTC CCA ATG GAG CTG CGG CAG TTT CTG GCC CCT TGG        331
Tyr Ser Asp Ser Phe Pro Met Glu Leu Arg Gln Phe Leu Ala Pro Trp
             25                  30                  35

ATT GAG AGT CAA GAT TGG GCA TAT GCG GCC AGC AAA GAA TCA CAT GCC        379
Ile Glu Ser Gln Asp Trp Ala Tyr Ala Ala Ser Lys Glu Ser His Ala
         40                  45                  50

ACT TTG GTG TTT CAT AAT CTC CTG GGA GAG ATT GAC CAG CAG TAT AGC        427
Thr Leu Val Phe His Asn Leu Leu Gly Glu Ile Asp Gln Gln Tyr Ser
     55                  60                  65

CGC TTC CTG CAA GAG TCG AAT GTT CTC TAT CAG CAC AAT CTA CGA AGA        475
Arg Phe Leu Gln Glu Ser Asn Val Leu Tyr Gln His Asn Leu Arg Arg
 70                  75                  80                  85

ATC AAG CAG TTT CTT CAG AGC AGG TAT CTT GAG AAG CCA ATG GAG ATT        523
Ile Lys Gln Phe Leu Gln Ser Arg Tyr Leu Glu Lys Pro Met Glu Ile
             90                  95                 100
```

| | | | | | | | | | | | | | | | | |
|---|---|---|---|---|---|---|---|---|---|---|---|---|---|---|---|---|
| GCC | CGG | ATT | GTG | GCC | CGG | TGC | CTG | TGG | GAA | GAA | TCA | CGC | CTT | CTA | CAG | 571 |
| Ala | Arg | Ile | Val | Ala | Arg | Cys | Leu | Trp | Glu | Glu | Ser | Arg | Leu | Leu | Gln | |
| | | 105 | | | | | 110 | | | | | 115 | | | | |
| ACT | GCA | GCC | ACT | GCG | GCC | CAG | CAA | GGG | GGC | CAG | GCC | AAC | CAC | CCC | ACA | 619 |
| Thr | Ala | Ala | Thr | Ala | Ala | Gln | Gln | Gly | Gly | Gln | Ala | Asn | His | Pro | Thr | |
| | | 120 | | | | | 125 | | | | | 130 | | | | |
| GCA | GCC | GTG | GTG | ACG | GAG | AAG | CAG | CAG | ATG | CTG | GAG | CAG | CAC | CTT | CAG | 667 |
| Ala | Ala | Val | Val | Thr | Glu | Lys | Gln | Gln | Met | Leu | Glu | Gln | His | Leu | Gln | |
| | 135 | | | | | 140 | | | | | 145 | | | | | |
| GAT | GTC | CGG | AAG | AGA | GTG | CAG | GAT | CTA | GAA | CAG | AAA | ATG | AAA | GTG | GTA | 715 |
| Asp | Val | Arg | Lys | Arg | Val | Gln | Asp | Leu | Glu | Gln | Lys | Met | Lys | Val | Val | |
| 150 | | | | | 155 | | | | | 160 | | | | | 165 | |
| GAG | AAT | CTC | CAG | GAT | GAC | TTT | GAT | TTC | AAC | TAT | AAA | ACC | CTC | AAG | AGT | 763 |
| Glu | Asn | Leu | Gln | Asp | Asp | Phe | Asp | Phe | Asn | Tyr | Lys | Thr | Leu | Lys | Ser | |
| | | | | 170 | | | | | 175 | | | | | 180 | | |
| CAA | GGA | GAC | ATG | CAA | GAT | CTG | AAT | GGA | AAC | AAC | CAG | TCA | GTG | ACC | AGG | 811 |
| Gln | Gly | Asp | Met | Gln | Asp | Leu | Asn | Gly | Asn | Asn | Gln | Ser | Val | Thr | Arg | |
| | | | 185 | | | | | 190 | | | | | 195 | | | |
| CAG | AAG | ATG | CAG | CAG | CTG | GAA | CAG | ATG | CTC | ACT | GCG | CTG | GAC | CAG | ATG | 859 |
| Gln | Lys | Met | Gln | Gln | Leu | Glu | Gln | Met | Leu | Thr | Ala | Leu | Asp | Gln | Met | |
| | | 200 | | | | | 205 | | | | | 210 | | | | |
| CGG | AGA | AGC | ATC | GTG | AGT | GAG | CTG | GCG | GGG | CTT | TTG | TCA | GCG | ATG | GAG | 907 |
| Arg | Arg | Ser | Ile | Val | Ser | Glu | Leu | Ala | Gly | Leu | Leu | Ser | Ala | Met | Glu | |
| | 215 | | | | | 220 | | | | | 225 | | | | | |
| TAC | GTG | CAG | AAA | ACT | CTC | ACG | GAC | GAG | GAG | CTG | GCT | GAC | TGG | AAG | AGG | 955 |
| Tyr | Val | Gln | Lys | Thr | Leu | Thr | Asp | Glu | Glu | Leu | Ala | Asp | Trp | Lys | Arg | |
| 230 | | | | | 235 | | | | | 240 | | | | | 245 | |
| CGG | CAA | CAG | ATT | GCC | TGC | ATT | GGA | GGC | CCG | CCC | AAC | ATC | TGC | CTA | GAT | 1003 |
| Arg | Gln | Gln | Ile | Ala | Cys | Ile | Gly | Gly | Pro | Pro | Asn | Ile | Cys | Leu | Asp | |
| | | | | 250 | | | | | 255 | | | | | 260 | | |
| CGG | CTA | GAA | AAC | TGG | ATA | ACG | TCA | TTA | GCA | GAA | TCT | CAA | CTT | CAG | ACC | 1051 |
| Arg | Leu | Glu | Asn | Trp | Ile | Thr | Ser | Leu | Ala | Glu | Ser | Gln | Leu | Gln | Thr | |
| | | | 265 | | | | | 270 | | | | | 275 | | | |
| CGT | CAA | CAA | ATT | AAG | AAA | CTG | GAG | GAG | TTG | CAC | CAA | AAA | GTT | TCC | TAC | 1099 |
| Arg | Gln | Gln | Ile | Lys | Lys | Leu | Glu | Glu | Leu | His | Gln | Lys | Val | Ser | Tyr | |
| | | 280 | | | | | 285 | | | | | 290 | | | | |
| AAA | GGG | GAC | CCC | ATT | GTA | CAG | CAC | CGG | CCG | ATG | CTG | GAG | GAG | AGG | ATC | 1147 |
| Lys | Gly | Asp | Pro | Ile | Val | Gln | His | Arg | Pro | Met | Leu | Glu | Glu | Arg | Ile | |
| | 295 | | | | | 300 | | | | | 305 | | | | | |
| GTG | GAG | CTG | TTC | AGA | AAC | TTA | ATG | AAA | AGT | GCC | TTT | GTG | GTG | GAG | CGG | 1195 |
| Val | Glu | Leu | Phe | Arg | Asn | Leu | Met | Lys | Ser | Ala | Phe | Val | Val | Glu | Arg | |
| 310 | | | | | 315 | | | | | 320 | | | | | 325 | |
| CAG | CCC | TGC | ATG | CCC | ATG | CAT | CCT | GAC | CGG | CCC | CTC | GTC | ATC | AAG | ACC | 1243 |
| Gln | Pro | Cys | Met | Pro | Met | His | Pro | Asp | Arg | Pro | Leu | Val | Ile | Lys | Thr | |
| | | | | 330 | | | | | 335 | | | | | 340 | | |
| GGC | GTC | CAG | TTC | ACT | ACT | AAA | GTC | AGG | TTG | CTG | GTC | AAG | TTC | CCT | GAG | 1291 |
| Gly | Val | Gln | Phe | Thr | Thr | Lys | Val | Arg | Leu | Leu | Val | Lys | Phe | Pro | Glu | |
| | | | 345 | | | | | 350 | | | | | 355 | | | |
| TTG | AAT | TAT | CAG | CTT | AAA | ATT | AAA | GTG | TGC | ATT | GAC | AAA | GAC | TCT | GGG | 1339 |
| Leu | Asn | Tyr | Gln | Leu | Lys | Ile | Lys | Val | Cys | Ile | Asp | Lys | Asp | Ser | Gly | |
| | | 360 | | | | | 365 | | | | | 370 | | | | |
| GAC | GTT | GCA | GCT | CTC | AGA | GGA | TCC | CGG | AAA | TTT | AAC | ATT | CTG | GGC | ACA | 1387 |
| Asp | Val | Ala | Ala | Leu | Arg | Gly | Ser | Arg | Lys | Phe | Asn | Ile | Leu | Gly | Thr | |
| | 375 | | | | | 380 | | | | | 385 | | | | | |
| AAC | ACA | AAA | GTG | ATG | AAC | ATG | GAA | GAA | TCC | AAC | AAC | GGC | AGC | CTC | TCT | 1435 |
| Asn | Thr | Lys | Val | Met | Asn | Met | Glu | Glu | Ser | Asn | Asn | Gly | Ser | Leu | Ser | |
| 390 | | | | | 395 | | | | | 400 | | | | | 405 | |
| GCA | GAA | TTC | AAA | CAC | TTG | ACC | CTG | AGG | GAG | CAG | AGA | TGT | GGG | AAT | GGG | 1483 |
| Ala | Glu | Phe | Lys | His | Leu | Thr | Leu | Arg | Glu | Gln | Arg | Cys | Gly | Asn | Gly | |
| | | | | 410 | | | | | 415 | | | | | 420 | | |

```
GGC CGA GCC AAT TGT GAT GCT TCC CTG ATT GTG ACT GAG GAG CTG CAC    1531
Gly Arg Ala Asn Cys Asp Ala Ser Leu Ile Val Thr Glu Glu Leu His
        425             430                 435

CTG ATC ACC TTT GAG ACC GAG GTG TAT CAC CAA GGT CTC AAG ATT GAC    1579
Leu Ile Thr Phe Glu Thr Glu Val Tyr His Gln Gly Leu Lys Ile Asp
        440             445                 450

CTA GAG ACC CAC TCC TTG TCA GTT GTG GTG ATC TCC AAC ATC TGT CAG    1627
Leu Glu Thr His Ser Leu Ser Val Val Val Ile Ser Asn Ile Cys Gln
        455             460                 465

ATG CCA AAT GCC TGG GCG TCC ATC CTG TGG TAC AAC ATG CTG ACC AAC    1675
Met Pro Asn Ala Trp Ala Ser Ile Leu Trp Tyr Asn Met Leu Thr Asn
470             475             480                 485

AAT CCC AAG AAT GTG AAC TTC TTC ACT AAG CCG CCA ATT GGA ACC TGG    1723
Asn Pro Lys Asn Val Asn Phe Phe Thr Lys Pro Pro Ile Gly Thr Trp
                490             495                 500

GAC CAA GTG GCC GAG GTG CTC AGC TGG CAG TTC TCG TCC ACC ACC AAG    1771
Asp Gln Val Ala Glu Val Leu Ser Trp Gln Phe Ser Ser Thr Thr Lys
                505             510                 515

CGG GGG CTG AGC ATC GAG CAG CTG ACA ACG CTG GCT GAG AAG CTC CTA    1819
Arg Gly Leu Ser Ile Glu Gln Leu Thr Thr Leu Ala Glu Lys Leu Leu
        520             525                 530

GGG CCT GGT GTG AAC TAC TCA GGG TGT CAG ATC ACA TGG GCT AAC TTC    1867
Gly Pro Gly Val Asn Tyr Ser Gly Cys Gln Ile Thr Trp Ala Asn Phe
535             540                 545

TGC AAA GAA AAC ATG GCT GGC AAG GGC TTC TCC TAC TGG GTC TGG CTA    1915
Cys Lys Glu Asn Met Ala Gly Lys Gly Phe Ser Tyr Trp Val Trp Leu
550             555             560                 565

GAC AAT ATC ATC GAC CTT GTG AAA AAG TAT ATC TTG GCC CTT TGG AAT    1963
Asp Asn Ile Ile Asp Leu Val Lys Lys Tyr Ile Leu Ala Leu Trp Asn
                570             575                 580

GAA GGG TAC ATC ATG GGT TTC ATC AGC AAG GAG CGG GAG CGG GCC ATC    2011
Glu Gly Tyr Ile Met Gly Phe Ile Ser Lys Glu Arg Glu Arg Ala Ile
                585             590                 595

TTG AGC ACT AAG CCC CCA GGC ACC TTC CTG CTG CGC TTC AGT GAA AGC    2059
Leu Ser Thr Lys Pro Pro Gly Thr Phe Leu Leu Arg Phe Ser Glu Ser
        600             605                 610

AGC AAA GAA GGA GGC GTC ACT TTC ACT TGG GTG GAG AAG GAC ATC AGC    2107
Ser Lys Glu Gly Gly Val Thr Phe Thr Trp Val Glu Lys Asp Ile Ser
615             620                 625

GGT AAG ACC CAG ATC CAG TCC GTG GAA CCA TAC ACA AAG CAG CAG CTG    2155
Gly Lys Thr Gln Ile Gln Ser Val Glu Pro Tyr Thr Lys Gln Gln Leu
630             635             640                 645

AAC AAC ATG TCA TTT GCT GAA ATC ATC ATG GGC TAT AAG ATC ATG GAT    2203
Asn Asn Met Ser Phe Ala Glu Ile Ile Met Gly Tyr Lys Ile Met Asp
                650             655                 660

GCT ACC AAT ATC CTG TTG TCT CCA CTT GTC TAT CTC TAT CCT GAC ATT    2251
Ala Thr Asn Ile Leu Leu Ser Pro Leu Val Tyr Leu Tyr Pro Asp Ile
                665             670                 675

CCC AAG GAG GAG GCA TTC GGG AAG TAT TGT CGG CCA GAG AGC CAG GAG    2299
Pro Lys Glu Glu Ala Phe Gly Lys Tyr Cys Arg Pro Glu Ser Gln Glu
        680             685                 690

CAT CCT GAA GCT GAC CCA GGT AGC GCT GCC CCA TAC CTG AAG ACC AAG    2347
His Pro Glu Ala Asp Pro Gly Ser Ala Ala Pro Tyr Leu Lys Thr Lys
        695             700                 705

TTT ATC TGT GTG ACA CCA ACG ACC TGC AGC AAT ACC ATT GAC CTG CCG    2395
Phe Ile Cys Val Thr Pro Thr Thr Cys Ser Asn Thr Ile Asp Leu Pro
710             715                 720                 725

ATG TCC CCC CGC GCT TTA GAT TCA TTG ATG CAG TTT GGA AAT AAT GGT    2443
Met Ser Pro Arg Ala Leu Asp Ser Leu Met Gln Phe Gly Asn Asn Gly
                730             735                 740
```

```
GAA GGT GCT GAA CCC TCA GCA GGA GGG CAG TTT GAG TCC CTC ACC TTT        2491
Glu Gly Ala Glu Pro Ser Ala Gly Gly Gln Phe Glu Ser Leu Thr Phe
            745                 750                 755

GAC ATG GAG TTG ACC TCG GAG TGC GCT ACC TCC CCC ATG TGAGGAGCTG         2540
Asp Met Glu Leu Thr Ser Glu Cys Ala Thr Ser Pro Met
        760                 765                 770

AGAACGGAAG CTGCAGAAAG ATACGACTGA GGCGCCTACC TGCATTCTGC CACCCCTCAC      2600

ACAGCCAAAC CCCAGATCAT CTGAAACTAC TAACTTTGTG GTTCCAGATT TTTTTAATC       2660

TCCTACTTCT GCTATCTTTG AGCAATCTGG GCACTTTTAA AAATAGAGAA ATGAGTGAAT      2720

GTGGGTGATC TGCTTTTATC TAAATGCAAA TAAGGATGTG TTCTCTGAGA CCCATGATCA      2780

GGGGATG                                                                2787
```

( 2 ) INFORMATION FOR SEQ ID NO:5:

( i ) SEQUENCE CHARACTERISTICS:
        ( A ) LENGTH: 770 amino acids
        ( B ) TYPE: amino acid
        ( D ) TOPOLOGY: linear ( i i ) MOLECULE TYPE: protein ( x i ) SEQUENCE DESCRIPTION: SEQ ID NO:5:

```
Met Ala Gln Trp Asn Gln Leu Gln Gln Leu Asp Thr Arg Tyr Leu Glu
 1               5                  10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
        35                  40                  45

Lys Glu Ser His Ala Thr Leu Val Phe His Asn Leu Leu Gly Glu Ile
 50                  55                  60

Asp Gln Gln Tyr Ser Arg Phe Leu Gln Glu Ser Asn Val Leu Tyr Gln
 65                  70                  75                  80

His Asn Leu Arg Arg Ile Lys Gln Phe Leu Gln Ser Arg Tyr Leu Glu
            85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
130                 135                 140

Glu Gln His Leu Gln Asp Val Arg Lys Arg Val Gln Asp Leu Glu Gln
145                 150                 155                 160

Lys Met Lys Val Val Glu Asn Leu Gln Asp Asp Phe Asp Phe Asn Tyr
                165                 170                 175

Lys Thr Leu Lys Ser Gln Gly Asp Met Gln Asp Leu Asn Gly Asn Asn
            180                 185                 190

Gln Ser Val Thr Arg Gln Lys Met Gln Gln Leu Glu Gln Met Leu Thr
        195                 200                 205

Ala Leu Asp Gln Met Arg Arg Ser Ile Val Ser Glu Leu Ala Gly Leu
210                 215                 220

Leu Ser Ala Met Glu Tyr Val Gln Lys Thr Leu Thr Asp Glu Glu Leu
225                 230                 235                 240

Ala Asp Trp Lys Arg Arg Gln Gln Ile Ala Cys Ile Gly Gly Pro Pro
                245                 250                 255

Asn Ile Cys Leu Asp Arg Leu Glu Asn Trp Ile Thr Ser Leu Ala Glu
```

|     |     |     |     |     |     |     | 260 |     |     |     |     | 265 |     |     |     |     | 270 |     |     |
|-----|-----|-----|-----|-----|-----|-----|-----|-----|-----|-----|-----|-----|-----|-----|-----|-----|-----|-----|-----|

Ser Gln Leu Gln Thr Arg Gln Gln Ile Lys Lys Leu Glu Leu His
                275                 280                 285

Gln Lys Val Ser Tyr Lys Gly Asp Pro Ile Val Gln His Arg Pro Met
    290                 295                 300

Leu Glu Glu Arg Ile Val Glu Leu Phe Arg Asn Leu Met Lys Ser Ala
305                 310                 315                 320

Phe Val Val Glu Arg Gln Pro Cys Met Pro Met His Pro Asp Arg Pro
                325                 330                 335

Leu Val Ile Lys Thr Gly Val Gln Phe Thr Thr Lys Val Arg Leu Leu
                340                 345                 350

Val Lys Phe Pro Glu Leu Asn Tyr Gln Leu Lys Ile Lys Val Cys Ile
                355                 360                 365

Asp Lys Asp Ser Gly Asp Val Ala Ala Leu Arg Gly Ser Arg Lys Phe
    370                 375                 380

Asn Ile Leu Gly Thr Asn Thr Lys Val Met Asn Met Glu Glu Ser Asn
385                 390                 395                 400

Asn Gly Ser Leu Ser Ala Glu Phe Lys His Leu Thr Leu Arg Glu Gln
                405                 410                 415

Arg Cys Gly Asn Gly Gly Arg Ala Asn Cys Asp Ala Ser Leu Ile Val
                420                 425                 430

Thr Glu Glu Leu His Leu Ile Thr Phe Glu Thr Glu Val Tyr His Gln
            435                 440                 445

Gly Leu Lys Ile Asp Leu Glu Thr His Ser Leu Ser Val Val Val Ile
    450                 455                 460

Ser Asn Ile Cys Gln Met Pro Asn Ala Trp Ala Ser Ile Leu Trp Tyr
465                 470                 475                 480

Asn Met Leu Thr Asn Asn Pro Lys Asn Val Asn Phe Phe Thr Lys Pro
                485                 490                 495

Pro Ile Gly Thr Trp Asp Gln Val Ala Glu Val Leu Ser Trp Gln Phe
            500                 505                 510

Ser Ser Thr Thr Lys Arg Gly Leu Ser Ile Glu Gln Leu Thr Thr Leu
            515                 520                 525

Ala Glu Lys Leu Leu Gly Pro Gly Val Asn Tyr Ser Gly Cys Gln Ile
    530                 535                 540

Thr Trp Ala Asn Phe Cys Lys Glu Asn Met Ala Gly Lys Gly Phe Ser
545                 550                 555                 560

Tyr Trp Val Trp Leu Asp Asn Ile Ile Asp Leu Val Lys Lys Tyr Ile
                565                 570                 575

Leu Ala Leu Trp Asn Glu Gly Tyr Ile Met Gly Phe Ile Ser Lys Glu
                580                 585                 590

Arg Glu Arg Ala Ile Leu Ser Thr Lys Pro Pro Gly Thr Phe Leu Leu
    595                 600                 605

Arg Phe Ser Glu Ser Ser Lys Glu Gly Gly Val Thr Phe Thr Trp Val
    610                 615                 620

Glu Lys Asp Ile Ser Gly Lys Thr Gln Ile Gln Ser Val Glu Pro Tyr
625                 630                 635                 640

Thr Lys Gln Gln Leu Asn Asn Met Ser Phe Ala Glu Ile Ile Met Gly
                645                 650                 655

Tyr Lys Ile Met Asp Ala Thr Asn Ile Leu Leu Ser Pro Leu Val Tyr
                660                 665                 670

Leu Tyr Pro Asp Ile Pro Lys Glu Glu Ala Phe Gly Lys Tyr Cys Arg
        675                 680                 685

| Pro | Glu | Ser | Gln | Glu | His | Pro | Glu | Ala | Asp | Pro | Gly | Ser | Ala | Ala | Pro |
|---|---|---|---|---|---|---|---|---|---|---|---|---|---|---|---|
| | 690 | | | | 695 | | | | | 700 | | | | | |

| Tyr | Leu | Lys | Thr | Lys | Phe | Ile | Cys | Val | Thr | Pro | Thr | Thr | Cys | Ser | Asn |
|---|---|---|---|---|---|---|---|---|---|---|---|---|---|---|---|
| 705 | | | | | 710 | | | | | 715 | | | | | 720 |

| Thr | Ile | Asp | Leu | Pro | Met | Ser | Pro | Arg | Ala | Leu | Asp | Ser | Leu | Met | Gln |
|---|---|---|---|---|---|---|---|---|---|---|---|---|---|---|---|
| | | | | 725 | | | | | 730 | | | | | 735 | |

| Phe | Gly | Asn | Asn | Gly | Glu | Gly | Ala | Glu | Pro | Ser | Ala | Gly | Gly | Gln | Phe |
|---|---|---|---|---|---|---|---|---|---|---|---|---|---|---|---|
| | | | | 740 | | | | | 745 | | | | 750 | | |

| Glu | Ser | Leu | Thr | Phe | Asp | Met | Glu | Leu | Thr | Ser | Glu | Cys | Ala | Thr | Ser |
|---|---|---|---|---|---|---|---|---|---|---|---|---|---|---|---|
| | | 755 | | | | | 760 | | | | | 765 | | | |

| Pro | Met |
|---|---|
| | 770 |

( 2 ) INFORMATION FOR SEQ ID NO:6:

( i ) SEQUENCE CHARACTERISTICS:
        ( A ) LENGTH: 2310 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:6:

```
ATGGCTCAGT GGAACCAGCT GCAGCAGCTG GACACACGCT ACCTGGAGCA GCTGCACCAG      60
CTGTACAGCG ACAGCTTCCC CATGGAGCTG CGGCAGTTCC TGGCACCTTG GATTGAGAGT     120
CAAGACTGGG CATATGCAGC CAGCAAAGAG TCACATGCCA CGTTGGTGTT TCATAATCTC     180
TTGGGTGAAA TTGACCAGCA ATATAGCCGA TTCCTGCAAG AGTCCAATGT CCTCTATCAG     240
CACAACCTTC GAAGAATCAA GCAGTTTCTG CAGAGCAGGT ATCTTGAGAA GCCAATGGAA     300
ATTGCCCGGA TCGTGGCCCG ATGCCTGTGG GAAGAGTCTC GCCTCCTCCA GACGGCAGCC     360
ACGGCAGCCC AGCAAGGGGG CCAGGCCAAC CACCCAACAG CTGCCGTAGT GACAGAGAAG     420
CAGCAGATGT GGAGCAGCA TCTTCAGGAT GTCCGGAAGC GAGTGCAGGA TCTAGAACAG     480
AAAATGAAGG TGGTGGAGAA CCTCCAGGAC GACTTTGATT TCAACTACAA AACCCTCAAG     540
AGCCAAGGAG ACATGCAGGA TCTGAATGGA ACAACCAGT CTGTGACCAG ACAGAAGATG     600
CAGCAGCTGG AACAGATGCT CACAGCCCTG GACCAGATGC GGAGAAGCAT TGTGAGTGAG     660
CTGGCGGGGC TCTTGTCAGC AATGGAGTAC GTGCAGAAGA CACTGACTGA TGAAGAGCTG     720
GCTGACTGGA AGAGGCGGCA GCAGATCGCG TGCATCGGAG GCCCTCCCAA CATCTGCCTG     780
GACCGTCTGG AAAACTGGAT AACTTCATTA GCAGAATCTC AACTTCAGAC CCGCCAACAA     840
ATTAAGAAAC TGGAGGAGCT GCAGCAGAAA GTGTCCTACA AGGGCGACCC TATCGTGCAG     900
CACCGGCCCA TGCTGGAGGA GAGGATCGTG GAGCTGTTCA GAAACTTAAT GAAGAGTGCC     960
TTCGTGGTGG AGCGGCAGCC CTGCATGCCC ATGCACCCGG ACCGGCCCTT AGTCATCAAG    1020
ACTGGTGTCC AGTTTACCAC GAAAGTCAGG TTGCTGGTCA AATTTCCTGA GTTGAATTAT    1080
CAGCTTAAAA TTAAAGTGTG CATTGATAAA GACTCTGGCG ATGTTGCTGC CCTCAGAGGG    1140
TCTCGGAAAT TTAACATTCT GGGCACGAAC ACAAAAGTGA TTAACATGGA GGAGTCTAAC    1200
AACGGCAGCC TGTCTGCAGA GTTCAAGCAC CTGACCCTTA GGGAGCAGAG ATGTGGGAAT    1260
GGAGGCCGTG CCAATTGTGA TGCCTCCTTG ATCGTGACTG AGGAGCTGCA CCTGATCACC    1320
TTCGAGACTG AGGTGTACCA CCAAGGCCTC AAGATTGACC TAGAGACCCA CTCCTTGCCA    1380
GTTGTGGTGA TCTCCAACAT CTGTCAGATG CCAAATGCTT GGGCATCAAT CCTGTGGTAT    1440
AACATGCTGA CCAATAACCC CAAGAACGTG AACTTCTTCA CTAAGCCGCC AATTGGAACC    1500
```

-continued

| | | | | | |
|---|---|---|---|---|---|
| TGGGACCAAG | TGGCCGAGGT | GCTCAGCTGG | CAGTTCTCGT | CCACCACCAA | GCGGGGGCTG | 1560
| AGCATCGAGC | AGCTGACAAC | GCTGGCTGAG | AAGCTCCTAG | GGCCTGGTGT | GAACTACTCA | 1620
| GGGTGTCAGA | TCACATGGGC | TAAATTCTGC | AAAGAAAACA | TGGCTGGCAA | GGGCTTCTCC | 1680
| TTCTGGGTCT | GGCTAGACAA | TATCATCGAC | CTTGTGAAAA | AGTATATCTT | GGCCCTTTGG | 1740
| AATGAAGGGT | ACATCATGGG | TTTCATCAGC | AAGGAGCGGG | AGCGGGCCAT | CCTAAGCACA | 1800
| AAGCCCCCGG | GCACCTTCCT | ACTGCGCTTC | AGCGAGAGCA | GCAAAGAAGG | AGGGGTCACT | 1860
| TTCACTTGGG | TGGAAAAGGA | CATCAGTGGC | AAGACCCAGA | TCCAGTCTGT | AGAGCCATAC | 1920
| ACCAAGCAGC | AGCTGAACAA | CATGTCATTT | GCTGAAATCA | TCATGGGCTA | TAAGATCATG | 1980
| GATGCGACCA | ACATCCTGGT | GTCTCCACTT | GTCTACCTCT | ACCCCGACAT | TCCCAAGGAG | 2040
| GAGGCATTTG | GAAAGTACTG | TAGGCCCGAG | AGCCAGGAGC | ACCCCGAAGC | CGACCCAGGT | 2100
| AGTGCTGCCC | CGTACCTGAA | GACCAAGTTC | ATCTGTGTGA | CACCAACGAC | CTGCAGCAAT | 2160
| ACCATTGACC | TGCCGATGTC | CCCCCGCACT | TTAGATTCAT | TGATGCAGTT | TGGAAATAAC | 2220
| GGTGAAGGTG | CTGAGCCCTC | AGCAGGAGGG | CAGTTTGAGT | CGCTCACGTT | TGACATGGAT | 2280
| CTGACCTCGG | AGTGTGCTAC | CTCCCCCATG | | | | 2310

( 2 ) INFORMATION FOR SEQ ID NO:7:

( i ) SEQUENCE CHARACTERISTICS:
        ( A ) LENGTH: 2652 base pairs
        ( B ) TYPE: nucleic acid
        ( C ) STRANDEDNESS: single
        ( D ) TOPOLOGY: linear ( i i ) MOLECULE TYPE: cDNA to mRNA ( x i ) SEQUENCE DESCRIPTION: SEQ ID NO:7:

| | | | | | |
|---|---|---|---|---|---|
| CTGGAGGGGC | TGTAATTCAG | CGGTTTCCGG | AGCTGCAGTG | TAGACAGGGA | GGGGGAACCT | 60
| GGGGTTCCGA | CGTCGCGGCG | GAGGGAACGA | GCCCTAACCG | GATCGCTGAG | GTACAACCCC | 120
| GCTCGGTGTC | GCCTGACCGC | GTCGGCTAGG | AGAGGCCAGG | CGGCCCTCGG | GAGCCCAGCA | 180
| GCTCGCGCCT | GGAGTCAGCG | CAGGCCGGCC | AGTCGGGCCT | CAGCCCCGGA | GACAGTCGAG | 240
| ACCCCTGACT | GCAGCAGGAT | GGCTCAGTGG | AACCAGCTGC | AGCAGCTGGA | CACACGCTAC | 300
| CTGGAGCAGC | TGCACCAGCT | GTACAGCGAC | AGCTTCCCCA | TGGAGCTGCG | GCAGTTCCTG | 360
| GCACCTTGGA | TTGAGAGTCA | AGACTGGGCA | TATGCAGCCA | GCAAAGAGTC | ACATGCCACG | 420
| TTGGTGTTTC | ATAATCTCTT | GGGTGAAATT | GACCAGCAAT | ATAGCCGATT | CCTGCAAGAG | 480
| TCCAATGTCC | TCTATCAGCA | CAACCTTCGA | AGAATCAAGC | AGTTTCTGCA | GAGCAGGTAT | 540
| CTTGAGAAGC | CAATGGAAAT | TGCCCGGATC | GTGGCCCGAT | GCCTGTGGGA | AGAGTCTCGC | 600
| CTCCTCCAGA | CGGCAGCCAC | GGCAGCCCAG | CAAGGGGCC | AGGCCAACCA | CCCAACAGCT | 660
| GCCGTAGTGA | CAGAGAAGCA | GCAGATGTTG | GAGCAGCATC | TTCAGGATGT | CCGGAAGCGA | 720
| GTGCAGGATC | TAGAACAGAA | AATGAAGGTG | GTGGAGAACC | TCCAGGACGA | CTTTGATTTC | 780
| AACTACAAAA | CCCTCAAGAG | CCAAGGAGAC | ATGCAGGATC | TGAATGGAAA | CAACCAGTCT | 840
| GTGACCAGAC | AGAAGATGCA | GCAGCTGGAA | CAGATGCTCA | CAGCCCTGGA | CCAGATGCGG | 900
| AGAAGCATTG | TGAGTGAGCT | GGCGGGGCTC | TTGTCAGCAA | TGGAGTACGT | GCAGAAGACA | 960
| CTGACTGATG | AAGAGCTGGC | TGACTGGAAG | AGGCGGCAGC | AGATCGCGTG | CATCGGAGGC | 1020
| CCTCCCAACA | TCTGCCTGGA | CCGTCTGGAA | AACTGGATAA | CTTCATTAGC | AGAATCTCAA | 1080
| CTTCAGACCC | GCCAACAAAT | TAAGAAACTG | GAGGAGCTGC | AGCAGAAAGT | GTCCTACAAG | 1140

-continued

| | | | | | |
|---|---|---|---|---|---|
| GGCGACCCTA | TCGTGCAGCA | CCGGCCCATG | CTGGAGGAGA | GGATCGTGGA | GCTGTTCAGA | 1200
| AACTTAATGA | AGAGTGCCTT | CGTGGTGGAG | CGGCAGCCCT | GCATGCCCAT | GCACCCGGAC | 1260
| CGGCCCTTAG | TCATCAAGAC | TGGTGTCCAG | TTTACCACGA | AAGTCAGGTT | GCTGGTCAAA | 1320
| TTTCCTGAGT | TGAATTATCA | GCTTAAAATT | AAAGTGTGCA | TTGATAAAGA | CTCTGGCGAT | 1380
| GTTGCTGCCC | TCAGAGGGTC | TCGGAAATTT | AACATTCTGG | GCACGAACAC | AAAAGTGATT | 1440
| AACATGGAGG | AGTCTAACAA | CGGCAGCCTG | TCTGCAGAGT | TCAAGCACCT | GACCCTTAGG | 1500
| GAGCAGAGAT | GTGGGAATGG | AGGCCGTGCC | AATTGTGATG | CCTCCTTGAT | CGTGACTGAG | 1560
| GAGCTGCACC | TGATCACCTT | CGAGACTGAG | GTGTACCACC | AAGGCCTCAA | GATTGACCTA | 1620
| GAGACCCACT | CCTTGCCAGT | TGTGGTGATC | TCCAACATCT | GTCAGATGCC | AAATGCTTGG | 1680
| GCATCAATCC | TGTGGTATAA | CATGCTGACC | AATAACCCCA | AGAACGTGAA | CTTCTTCACT | 1740
| AAGCCGCCAA | TTGGAACCTG | GGACCAAGTG | GCCGAGGTGC | TCAGCTGGCA | GTTCTCGTCC | 1800
| ACCACCAAGC | GGGGGCTGAG | CATCGAGCAG | CTGACAACGC | TGGCTGAGAA | GCTCCTAGGG | 1860
| CCTGGTGTGA | ACTACTCAGG | GTGTCAGATC | ACATGGGCTA | AATTCTGCAA | AGAAAACATG | 1920
| GCTGGCAAGG | GCTTCTCCTT | CTGGGTCTGG | CTAGACAATA | TCATCGACCT | TGTGAAAAAG | 1980
| TATATCTTGG | CCCTTTGGAA | TGAAGGGTAC | ATCATGGGTT | TCATCAGCAA | GGAGCGGGAG | 2040
| CGGGCCATCC | TAAGCACAAA | GCCCCCGGGC | ACCTTCCTAC | TGCGCTTCAG | CGAGAGCAGC | 2100
| AAAGAAGGAG | GGGTCACTTT | CACTTGGGTG | GAAAGGACA | TCAGTGGCAA | GACCCAGATC | 2160
| CAGTCTGTAG | AGCCATACAC | CAAGCAGCAG | CTGAACAACA | TGTCATTTGC | TGAAATCATC | 2220
| ATGGGCTATA | AGATCATGGA | TGCGACCAAC | ATCCTGGTGT | CTCCACTTGT | CTACCTCTAC | 2280
| CCCGACATTC | CAAGGAGGA | GGCATTTGGA | AAGTACTGTA | GGCCCGAGAG | CCAGGAGCAC | 2340
| CCCGAAGCCG | ACCCAGGTAG | TGCTGCCCCG | TACCTGAAGA | CCAAGTTCAT | CTGTGTGACA | 2400
| CCAACGACCT | GCAGCAATAC | CATTGACCTG | CCGATGTCCC | CCGCACTTT | AGATTCATTG | 2460
| ATGCAGTTTG | GAAATAACGG | TGAAGGTGCT | GAGCCCTCAG | CAGGAGGGCA | GTTTGAGTCG | 2520
| CTCACGTTTG | ACATGGATCT | GACCTCGGAG | TGTGCTACCT | CCCCATGTG | AGGAGCTGAA | 2580
| ACCAGAAGCT | GCAGAGACGT | GACTTGAGAC | ACCTGCCCCG | TGCTCCACCC | CTAAGCAGCC | 2640
| GAACCCCATA | TC | | | | | 2652

( 2 ) INFORMATION FOR SEQ ID NO:8:

( i ) SEQUENCE CHARACTERISTICS:
        ( A ) LENGTH: 2652 base pairs
        ( B ) TYPE: nucleic acid
        ( C ) STRANDEDNESS: single
        ( D ) TOPOLOGY: linear ( i i ) MOLECULE TYPE: cDNA to mRNA ( v i ) ORIGINAL SOURCE:
        ( A ) ORGANISM: Mouse
        ( F ) TISSUE TYPE: Liver ( i x ) FEATURE:
        ( A ) NAME/KEY: CDS
        ( B ) LOCATION: 259..2568

( x i ) SEQUENCE DESCRIPTION: SEQ ID NO:8:

| | | | | | |
|---|---|---|---|---|---|
| CTGGAGGGGC | TGTAATTCAG | CGGTTTCCGG | AGCTGCAGTG | TAGACAGGGA | GGGGGAACCT | 60
| GGGGTTCCGA | CGTCGCGGCG | GAGGGAACGA | GCCCTAACCG | GATCGCTGAG | GTACAACCCC | 120
| GCTCGGTGTC | GCCTGACCGC | GTCGGCTAGG | AGAGGCCAGG | CGGCCCTCGG | GAGCCCAGCA | 180
| GCTCGCGCCT | GGAGTCAGCG | CAGGCCGGCC | AGTCGGGCCT | CAGCCCCGGA | GACAGTCGAG | 240

|  |  |  |  |  |  |  |  |  |  |  |  |  |  |  |  |  |
|---|---|---|---|---|---|---|---|---|---|---|---|---|---|---|---|---|
| ACCCCTGACT | GCAGCAGG | ATG<br>Met<br>1 | GCT<br>Ala | CAG<br>Gln | TGG<br>Trp | AAC<br>Asn<br>5 | CAG<br>Gln | CTG<br>Leu | CAG<br>Gln | CAG<br>Gln | CTG<br>Leu<br>10 | GAC<br>Asp | | | | 291 |
| ACA<br>Thr | CGC<br>Arg | TAC<br>Tyr | CTG<br>Leu<br>15 | GAG<br>Glu | CAG<br>Gln | CTG<br>Leu | CAC<br>His | CAG<br>Gln<br>20 | CTG<br>Leu | TAC<br>Tyr | AGC<br>Ser | GAC<br>Asp | AGC<br>Ser<br>25 | TTC<br>Phe | CCC<br>Pro | 339 |
| ATG<br>Met | GAG<br>Glu | CTG<br>Leu<br>30 | CGG<br>Arg | CAG<br>Gln | TTC<br>Phe | CTG<br>Leu | GCA<br>Ala<br>35 | CCT<br>Pro | TGG<br>Trp | ATT<br>Ile | GAG<br>Glu | AGT<br>Ser<br>40 | CAA<br>Gln | GAC<br>Asp | TGG<br>Trp | 387 |
| GCA<br>Ala | TAT<br>Tyr<br>45 | GCA<br>Ala | GCC<br>Ala | AGC<br>Ser | AAA<br>Lys | GAG<br>Glu<br>50 | TCA<br>Ser | CAT<br>His | GCC<br>Ala | ACG<br>Thr | TTG<br>Leu<br>55 | GTG<br>Val | TTT<br>Phe | CAT<br>His | AAT<br>Asn | 435 |
| CTC<br>Leu<br>60 | TTG<br>Leu | GGT<br>Gly | GAA<br>Glu | ATT<br>Ile | GAC<br>Asp<br>65 | CAG<br>Gln | CAA<br>Gln | TAT<br>Tyr | AGC<br>Ser | CGA<br>Arg<br>70 | TTC<br>Phe | CTG<br>Leu | CAA<br>Gln | GAG<br>Glu | TCC<br>Ser<br>75 | 483 |
| AAT<br>Asn | GTC<br>Val | CTC<br>Leu | TAT<br>Tyr | CAG<br>Gln<br>80 | CAC<br>His | AAC<br>Asn | CTT<br>Leu | CGA<br>Arg | AGA<br>Arg<br>85 | ATC<br>Ile | AAG<br>Lys | CAG<br>Gln | TTT<br>Phe | CTG<br>Leu<br>90 | CAG<br>Gln | 531 |
| AGC<br>Ser | AGG<br>Arg | TAT<br>Tyr | CTT<br>Leu<br>95 | GAG<br>Glu | AAG<br>Lys | CCA<br>Pro | ATG<br>Met | GAA<br>Glu<br>100 | ATT<br>Ile | GCC<br>Ala | CGG<br>Arg | ATC<br>Ile | GTG<br>Val<br>105 | GCC<br>Ala | CGA<br>Arg | 579 |
| TGC<br>Cys | CTG<br>Leu | TGG<br>Trp<br>110 | GAA<br>Glu | GAG<br>Glu | TCT<br>Ser | CGC<br>Arg | CTC<br>Leu<br>115 | CTC<br>Leu | CAG<br>Gln | ACG<br>Thr | GCA<br>Ala | GCC<br>Ala<br>120 | ACG<br>Thr | GCA<br>Ala | GCC<br>Ala | 627 |
| CAG<br>Gln | CAA<br>Gln<br>125 | GGG<br>Gly | GGC<br>Gly | CAG<br>Gln | GCC<br>Ala | AAC<br>Asn<br>130 | CAC<br>His | CCA<br>Pro | ACA<br>Thr | GCT<br>Ala | GCC<br>Ala<br>135 | GTA<br>Val | GTG<br>Val | ACA<br>Thr | GAG<br>Glu | 675 |
| AAG<br>Lys<br>140 | CAG<br>Gln | CAG<br>Gln | ATG<br>Met | TTG<br>Leu | GAG<br>Glu<br>145 | CAG<br>Gln | CAT<br>His | CTT<br>Leu | CAG<br>Gln | GAT<br>Asp<br>150 | GTC<br>Val | CGG<br>Arg | AAG<br>Lys | CGA<br>Arg | GTG<br>Val<br>155 | 723 |
| CAG<br>Gln | GAT<br>Asp | CTA<br>Leu | GAA<br>Glu | CAG<br>Gln<br>160 | AAA<br>Lys | ATG<br>Met | AAG<br>Lys | GTG<br>Val | GTG<br>Val<br>165 | GAG<br>Glu | AAC<br>Asn | CTC<br>Leu | CAG<br>Gln | GAC<br>Asp<br>170 | GAC<br>Asp | 771 |
| TTT<br>Phe | GAT<br>Asp | TTC<br>Phe | AAC<br>Asn<br>175 | TAC<br>Tyr | AAA<br>Lys | ACC<br>Thr | CTC<br>Leu | AAG<br>Lys<br>180 | AGC<br>Ser | CAA<br>Gln | GGA<br>Gly | GAC<br>Asp | ATG<br>Met<br>185 | CAG<br>Gln | GAT<br>Asp | 819 |
| CTG<br>Leu | AAT<br>Asn | GGA<br>Gly<br>190 | AAC<br>Asn | AAC<br>Asn | CAG<br>Gln | TCT<br>Ser | GTG<br>Val<br>195 | ACC<br>Thr | AGA<br>Arg | CAG<br>Gln | AAG<br>Lys | ATG<br>Met<br>200 | CAG<br>Gln | CAG<br>Gln | CTG<br>Leu | 867 |
| GAA<br>Glu | CAG<br>Gln | ATG<br>Met<br>205 | CTC<br>Leu | ACA<br>Thr | GCC<br>Ala | CTG<br>Leu | GAC<br>Asp<br>210 | CAG<br>Gln | ATG<br>Met | CGG<br>Arg | AGA<br>Arg | AGC<br>Ser<br>215 | ATT<br>Ile | GTG<br>Val | AGT<br>Ser | 915 |
| GAG<br>Glu<br>220 | CTG<br>Leu | GCG<br>Ala | GGG<br>Gly | CTC<br>Leu | TTG<br>Leu<br>225 | TCA<br>Ser | GCA<br>Ala | ATG<br>Met | GAG<br>Glu | TAC<br>Tyr<br>230 | GTG<br>Val | CAG<br>Gln | AAG<br>Lys | ACA<br>Thr | CTG<br>Leu<br>235 | 963 |
| ACT<br>Thr | GAT<br>Asp | GAA<br>Glu | GAG<br>Glu | CTG<br>Leu<br>240 | GCT<br>Ala | GAC<br>Asp | TGG<br>Trp | AAG<br>Lys | AGG<br>Arg<br>245 | CGG<br>Arg | CAG<br>Gln | CAG<br>Gln | ATC<br>Ile | GCG<br>Ala<br>250 | TGC<br>Cys | 1011 |
| ATC<br>Ile | GGA<br>Gly | GGC<br>Gly | CCT<br>Pro<br>255 | CCC<br>Pro | AAC<br>Asn | ATC<br>Ile | TGC<br>Cys | CTG<br>Leu<br>260 | GAC<br>Asp | CGT<br>Arg | CTG<br>Leu | GAA<br>Glu | AAC<br>Asn<br>265 | TGG<br>Trp | ATA<br>Ile | 1059 |
| ACT<br>Thr | TCA<br>Ser | TTA<br>Leu<br>270 | GCA<br>Ala | GAA<br>Glu | TCT<br>Ser | CAA<br>Gln | CTT<br>Leu<br>275 | CAG<br>Gln | ACC<br>Thr | CGC<br>Arg | CAA<br>Gln | CAA<br>Gln<br>280 | ATT<br>Ile | AAG<br>Lys | AAA<br>Lys | 1107 |
| CTG<br>Leu | GAG<br>Glu<br>285 | GAG<br>Glu | CTG<br>Leu | CAG<br>Gln | CAG<br>Gln | AAA<br>Lys<br>290 | GTG<br>Val | TCC<br>Ser | TAC<br>Tyr | AAG<br>Lys | GGC<br>Gly<br>295 | GAC<br>Asp | CCT<br>Pro | ATC<br>Ile | GTG<br>Val | 1155 |
| CAG<br>Gln | CAC<br>His<br>300 | CGG<br>Arg | CCC<br>Pro | ATG<br>Met | CTG<br>Leu | GAG<br>Glu<br>305 | GAG<br>Glu | AGG<br>Arg | ATC<br>Ile | GTG<br>Val | GAG<br>Glu<br>310 | CTG<br>Leu | TTC<br>Phe | AGA<br>Arg | AAC<br>Asn<br>315 | 1203 |

```
TTA ATG AAG AGT GCC TTC GTG GTG GAG CGG CAG CCC TGC ATG CCC ATG    1251
Leu Met Lys Ser Ala Phe Val Val Glu Arg Gln Pro Cys Met Pro Met
            320             325             330

CAC CCG GAC CGG CCC TTA GTC ATC AAG ACT GGT GTC CAG TTT ACC ACG    1299
His Pro Asp Arg Pro Leu Val Ile Lys Thr Gly Val Gln Phe Thr Thr
        335             340             345

AAA GTC AGG TTG CTG GTC AAA TTT CCT GAG TTG AAT TAT CAG CTT AAA    1347
Lys Val Arg Leu Leu Val Lys Phe Pro Glu Leu Asn Tyr Gln Leu Lys
        350             355             360

ATT AAA GTG TGC ATT GAT AAA GAC TCT GGC GAT GTT GCT GCC CTC AGA    1395
Ile Lys Val Cys Ile Asp Lys Asp Ser Gly Asp Val Ala Ala Leu Arg
        365             370             375

GGG TCT CGG AAA TTT AAC ATT CTG GGC ACG AAC ACA AAA GTG ATT AAC    1443
Gly Ser Arg Lys Phe Asn Ile Leu Gly Thr Asn Thr Lys Val Ile Asn
380             385             390             395

ATG GAG GAG TCT AAC AAC GGC AGC CTG TCT GCA GAG TTC AAG CAC CTG    1491
Met Glu Glu Ser Asn Asn Gly Ser Leu Ser Ala Glu Phe Lys His Leu
            400             405             410

ACC CTT AGG GAG CAG AGA TGT GGG AAT GGA GGC CGT GCC AAT TGT GAT    1539
Thr Leu Arg Glu Gln Arg Cys Gly Asn Gly Gly Arg Ala Asn Cys Asp
        415             420             425

GCC TCC TTG ATC GTG ACT GAG GAG CTG CAC CTG ATC ACC TTC GAG ACT    1587
Ala Ser Leu Ile Val Thr Glu Glu Leu His Leu Ile Thr Phe Glu Thr
        430             435             440

GAG GTG TAC CAC CAA GGC CTC AAG ATT GAC CTA GAG ACC CAC TCC TTG    1635
Glu Val Tyr His Gln Gly Leu Lys Ile Asp Leu Glu Thr His Ser Leu
        445             450             455

CCA GTT GTG GTG ATC TCC AAC ATC TGT CAG ATG CCA AAT GCT TGG GCA    1683
Pro Val Val Val Ile Ser Asn Ile Cys Gln Met Pro Asn Ala Trp Ala
460             465             470             475

TCA ATC CTG TGG TAT AAC ATG CTG ACC AAT AAC CCC AAG AAC GTG AAC    1731
Ser Ile Leu Trp Tyr Asn Met Leu Thr Asn Asn Pro Lys Asn Val Asn
            480             485             490

TTC TTC ACT AAG CCG CCA ATT GGA ACC TGG GAC CAA GTG GCC GAG GTG    1779
Phe Phe Thr Lys Pro Pro Ile Gly Thr Trp Asp Gln Val Ala Glu Val
        495             500             505

CTC AGC TGG CAG TTC TCG TCC ACC ACC AAG CGG GGG CTG AGC ATC GAG    1827
Leu Ser Trp Gln Phe Ser Ser Thr Thr Lys Arg Gly Leu Ser Ile Glu
        510             515             520

CAG CTG ACA ACG CTG GCT GAG AAG CTC CTA GGG CCT GGT GTG AAC TAC    1875
Gln Leu Thr Thr Leu Ala Glu Lys Leu Leu Gly Pro Gly Val Asn Tyr
        525             530             535

TCA GGG TGT CAG ATC ACA TGG GCT AAA TTC TGC AAA GAA AAC ATG GCT    1923
Ser Gly Cys Gln Ile Thr Trp Ala Lys Phe Cys Lys Glu Asn Met Ala
540             545             550             555

GGC AAG GGC TTC TCC TTC TGG GTC TGG CTA GAC AAT ATC ATC GAC CTT    1971
Gly Lys Gly Phe Ser Phe Trp Val Trp Leu Asp Asn Ile Ile Asp Leu
            560             565             570

GTG AAA AAG TAT ATC TTG GCC CTT TGG AAT GAA GGG TAC ATC ATG GGT    2019
Val Lys Lys Tyr Ile Leu Ala Leu Trp Asn Glu Gly Tyr Ile Met Gly
            575             580             585

TTC ATC AGC AAG GAG CGG GAG CGG GCC ATC CTA AGC ACA AAG CCC CCG    2067
Phe Ile Ser Lys Glu Arg Glu Arg Ala Ile Leu Ser Thr Lys Pro Pro
        590             595             600

GGC ACC TTC CTA CTG CGC TTC AGC GAG AGC AGC AAA GAA GGA GGG GTC    2115
Gly Thr Phe Leu Leu Arg Phe Ser Glu Ser Ser Lys Glu Gly Gly Val
        605             610             615

ACT TTC ACT TGG GTG GAA AAG GAC ATC AGT GGC AAG ACC CAG ATC CAG    2163
Thr Phe Thr Trp Val Glu Lys Asp Ile Ser Gly Lys Thr Gln Ile Gln
620             625             630             635
```

```
TCT GTA GAG CCA TAC ACC AAG CAG CAG CTG AAC AAC ATG TCA TTT GCT        2211
Ser Val Glu Pro Tyr Thr Lys Gln Gln Leu Asn Asn Met Ser Phe Ala
            640             645                 650

GAA ATC ATC ATG GGC TAT AAG ATC ATG GAT GCG ACC AAC ATC CTG GTG        2259
Glu Ile Ile Met Gly Tyr Lys Ile Met Asp Ala Thr Asn Ile Leu Val
            655             660                 665

TCT CCA CTT GTC TAC CTC TAC CCC GAC ATT CCC AAG GAG GAG GCA TTT        2307
Ser Pro Leu Val Tyr Leu Tyr Pro Asp Ile Pro Lys Glu Glu Ala Phe
            670             675                 680

GGA AAG TAC TGT AGG CCC GAG AGC CAG GAG CAC CCC GAA GCC GAC CCA        2355
Gly Lys Tyr Cys Arg Pro Glu Ser Gln Glu His Pro Glu Ala Asp Pro
            685             690                 695

GGT AGT GCT GCC CCG TAC CTG AAG ACC AAG TTC ATC TGT GTG ACA CCA        2403
Gly Ser Ala Ala Pro Tyr Leu Lys Thr Lys Phe Ile Cys Val Thr Pro
700             705             710                 715

ACG ACC TGC AGC AAT ACC ATT GAC CTG CCG ATG TCC CCC CGC ACT TTA        2451
Thr Thr Cys Ser Asn Thr Ile Asp Leu Pro Met Ser Pro Arg Thr Leu
            720             725                 730

GAT TCA TTG ATG CAG TTT GGA AAT AAC GGT GAA GGT GCT GAG CCC TCA        2499
Asp Ser Leu Met Gln Phe Gly Asn Asn Gly Glu Gly Ala Glu Pro Ser
            735             740                 745

GCA GGA GGG CAG TTT GAG TCG CTC ACG TTT GAC ATG GAT CTG ACC TCG        2547
Ala Gly Gly Gln Phe Glu Ser Leu Thr Phe Asp Met Asp Leu Thr Ser
            750             755                 760

GAG TGT GCT ACC TCC CCC ATG TGAGGAGCTG AAACCAGAAG CTGCAGAGAC           2598
Glu Cys Ala Thr Ser Pro Met
765             770

GTGACTTGAG ACACCTGCCC CGTGCTCCAC CCCTAAGCAG CCGAACCCCA TATC             2652
```

( 2 ) INFORMATION FOR SEQ ID NO:9:

( i ) SEQUENCE CHARACTERISTICS:
( A ) LENGTH: 770 amino acids
( B ) TYPE: amino acid
( D ) TOPOLOGY: linear ( i i ) MOLECULE TYPE: protein ( x i ) SEQUENCE DESCRIPTION: SEQ ID NO:9:

```
Met Ala Gln Trp Asn Gln Leu Gln Gln Leu Asp Thr Arg Tyr Leu Glu
1               5                   10                  15

Gln Leu His Gln Leu Tyr Ser Asp Ser Phe Pro Met Glu Leu Arg Gln
            20                  25                  30

Phe Leu Ala Pro Trp Ile Glu Ser Gln Asp Trp Ala Tyr Ala Ala Ser
            35                  40                  45

Lys Glu Ser His Ala Thr Leu Val Phe His Asn Leu Leu Gly Glu Ile
        50                  55                  60

Asp Gln Gln Tyr Ser Arg Phe Leu Gln Glu Ser Asn Val Leu Tyr Gln
65                  70                  75                  80

His Asn Leu Arg Arg Ile Lys Gln Phe Leu Gln Ser Arg Tyr Leu Glu
            85                  90                  95

Lys Pro Met Glu Ile Ala Arg Ile Val Ala Arg Cys Leu Trp Glu Glu
            100                 105                 110

Ser Arg Leu Leu Gln Thr Ala Ala Thr Ala Ala Gln Gln Gly Gly Gln
        115                 120                 125

Ala Asn His Pro Thr Ala Ala Val Val Thr Glu Lys Gln Gln Met Leu
        130                 135                 140

Glu Gln His Leu Gln Asp Val Arg Lys Arg Val Gln Asp Leu Glu Gln
145                 150                 155                 160
```

-continued

| | | | | | | | | | | | | | | |
|---|---|---|---|---|---|---|---|---|---|---|---|---|---|---|
| Lys | Met | Lys | Val | Val | Glu | Asn | Leu | Gln | Asp | Phe | Asp | Phe | Asn | Tyr |
| | | | | 165 | | | | 170 | | | | | 175 | |
| Lys | Thr | Leu | Lys | Ser | Gln | Gly | Asp | Met | Gln | Asp | Leu | Asn | Gly | Asn | Asn |
| | | | 180 | | | | | 185 | | | | | 190 | | |
| Gln | Ser | Val | Thr | Arg | Gln | Lys | Met | Gln | Gln | Leu | Glu | Gln | Met | Leu | Thr |
| | | 195 | | | | 200 | | | | | 205 | | | | |
| Ala | Leu | Asp | Gln | Met | Arg | Arg | Ser | Ile | Val | Ser | Glu | Leu | Ala | Gly | Leu |
| | 210 | | | | | 215 | | | | | 220 | | | | |
| Leu | Ser | Ala | Met | Glu | Tyr | Val | Gln | Lys | Thr | Leu | Thr | Asp | Glu | Glu | Leu |
| 225 | | | | | 230 | | | | | 235 | | | | | 240 |
| Ala | Asp | Trp | Lys | Arg | Arg | Gln | Gln | Ile | Ala | Cys | Ile | Gly | Gly | Pro | Pro |
| | | | | 245 | | | | | 250 | | | | | 255 | |
| Asn | Ile | Cys | Leu | Asp | Arg | Leu | Glu | Asn | Trp | Ile | Thr | Ser | Leu | Ala | Glu |
| | | | 260 | | | | | 265 | | | | | 270 | | |
| Ser | Gln | Leu | Gln | Thr | Arg | Gln | Gln | Ile | Lys | Lys | Leu | Glu | Glu | Leu | Gln |
| | | 275 | | | | 280 | | | | | 285 | | | | |
| Gln | Lys | Val | Ser | Tyr | Lys | Gly | Asp | Pro | Ile | Val | Gln | His | Arg | Pro | Met |
| | 290 | | | | | 295 | | | | | 300 | | | | |
| Leu | Glu | Glu | Arg | Ile | Val | Glu | Leu | Phe | Arg | Asn | Leu | Met | Lys | Ser | Ala |
| 305 | | | | | 310 | | | | | 315 | | | | | 320 |
| Phe | Val | Val | Glu | Arg | Gln | Pro | Cys | Met | Pro | Met | His | Pro | Asp | Arg | Pro |
| | | | | 325 | | | | | 330 | | | | | 335 | |
| Leu | Val | Ile | Lys | Thr | Gly | Val | Gln | Phe | Thr | Thr | Lys | Val | Arg | Leu | Leu |
| | | | 340 | | | | | 345 | | | | | 350 | | |
| Val | Lys | Phe | Pro | Glu | Leu | Asn | Tyr | Gln | Leu | Lys | Ile | Lys | Val | Cys | Ile |
| | | 355 | | | | | 360 | | | | | 365 | | | |
| Asp | Lys | Asp | Ser | Gly | Asp | Val | Ala | Ala | Leu | Arg | Gly | Ser | Arg | Lys | Phe |
| | 370 | | | | | 375 | | | | | 380 | | | | |
| Asn | Ile | Leu | Gly | Thr | Asn | Thr | Lys | Val | Ile | Asn | Met | Glu | Glu | Ser | Asn |
| 385 | | | | | 390 | | | | | 395 | | | | | 400 |
| Asn | Gly | Ser | Leu | Ser | Ala | Glu | Phe | Lys | His | Leu | Thr | Leu | Arg | Glu | Gln |
| | | | | 405 | | | | | 410 | | | | | 415 | |
| Arg | Cys | Gly | Asn | Gly | Gly | Arg | Ala | Asn | Cys | Asp | Ala | Ser | Leu | Ile | Val |
| | | | 420 | | | | | 425 | | | | | 430 | | |
| Thr | Glu | Glu | Leu | His | Leu | Ile | Thr | Phe | Glu | Thr | Glu | Val | Tyr | His | Gln |
| | | 435 | | | | | 440 | | | | | 445 | | | |
| Gly | Leu | Lys | Ile | Asp | Leu | Glu | Thr | His | Ser | Leu | Pro | Val | Val | Val | Ile |
| | 450 | | | | | 455 | | | | | 460 | | | | |
| Ser | Asn | Ile | Cys | Gln | Met | Pro | Asn | Ala | Trp | Ala | Ser | Ile | Leu | Trp | Tyr |
| 465 | | | | | 470 | | | | | 475 | | | | | 480 |
| Asn | Met | Leu | Thr | Asn | Asn | Pro | Lys | Asn | Val | Asn | Phe | Phe | Thr | Lys | Pro |
| | | | | 485 | | | | | 490 | | | | | 495 | |
| Pro | Ile | Gly | Thr | Trp | Asp | Gln | Val | Ala | Glu | Val | Leu | Ser | Trp | Gln | Phe |
| | | | 500 | | | | | 505 | | | | | 510 | | |
| Ser | Ser | Thr | Thr | Lys | Arg | Gly | Leu | Ser | Ile | Glu | Gln | Leu | Thr | Thr | Leu |
| | | 515 | | | | 520 | | | | | 525 | | | | |
| Ala | Glu | Lys | Leu | Leu | Gly | Pro | Gly | Val | Asn | Tyr | Ser | Gly | Cys | Gln | Ile |
| | 530 | | | | | 535 | | | | | 540 | | | | |
| Thr | Trp | Ala | Lys | Phe | Cys | Lys | Glu | Asn | Met | Ala | Gly | Lys | Gly | Phe | Ser |
| 545 | | | | | 550 | | | | | 555 | | | | | 560 |
| Phe | Trp | Val | Trp | Leu | Asp | Asn | Ile | Ile | Asp | Leu | Val | Lys | Lys | Tyr | Ile |
| | | | | 565 | | | | | 570 | | | | | 575 | |
| Leu | Ala | Leu | Trp | Asn | Glu | Gly | Tyr | Ile | Met | Gly | Phe | Ile | Ser | Lys | Glu |

-continued

|  |  |  | 580 |  |  |  |  | 585 |  |  |  | 590 |  |  |
|---|---|---|---|---|---|---|---|---|---|---|---|---|---|---|
| Arg | Glu | Arg<br>595 | Ala | Ile | Leu | Ser | Thr<br>600 | Lys | Pro | Pro | Gly | Thr<br>605 | Phe | Leu | Leu |
| Arg | Phe<br>610 | Ser | Glu | Ser | Ser | Lys<br>615 | Glu | Gly | Gly | Val | Thr<br>620 | Phe | Thr | Trp | Val |
| Glu<br>625 | Lys | Asp | Ile | Ser | Gly<br>630 | Lys | Thr | Gln | Ile | Gln<br>635 | Ser | Val | Glu | Pro | Tyr<br>640 |
| Thr | Lys | Gln | Gln | Leu<br>645 | Asn | Asn | Met | Ser | Phe<br>650 | Ala | Glu | Ile | Ile | Met<br>655 | Gly |
| Tyr | Lys | Ile | Met<br>660 | Asp | Ala | Thr | Asn | Ile<br>665 | Leu | Val | Ser | Pro | Leu<br>670 | Val | Tyr |
| Leu | Tyr | Pro<br>675 | Asp | Ile | Pro | Lys | Glu<br>680 | Glu | Ala | Phe | Gly | Lys<br>685 | Tyr | Cys | Arg |
| Pro | Glu<br>690 | Ser | Gln | Glu | His | Pro<br>695 | Glu | Ala | Asp | Pro | Gly<br>700 | Ser | Ala | Ala | Pro |
| Tyr<br>705 | Leu | Lys | Thr | Lys | Phe<br>710 | Ile | Cys | Val | Thr | Pro<br>715 | Thr | Thr | Cys | Ser | Asn<br>720 |
| Thr | Ile | Asp | Leu | Pro<br>725 | Met | Ser | Pro | Arg | Thr<br>730 | Leu | Asp | Ser | Leu | Met<br>735 | Gln |
| Phe | Gly | Asn | Asn<br>740 | Gly | Glu | Gly | Ala | Glu<br>745 | Pro | Ser | Ala | Gly | Gly<br>750 | Gln | Phe |
| Glu | Ser | Leu<br>755 | Thr | Phe | Asp | Met | Asp<br>760 | Leu | Thr | Ser | Glu | Cys<br>765 | Ala | Thr | Ser |
| Pro | Met<br>770 |  |  |  |  |  |  |  |  |  |  |  |  |  |  |

( 2 ) INFORMATION FOR SEQ ID NO:10:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "oligonucleotide"

( x i ) SEQUENCE DESCRIPTION: SEQ ID NO:10:

CCTTCCGGGA ATTC        14

( 2 ) INFORMATION FOR SEQ ID NO:11:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "degenerate oligonucleotide"

( x i ) SEQUENCE DESCRIPTION: SEQ ID NO:11:

ACNCARATHC ARTCNGT        17

NUCLEIC ACIDS ENCODING TRANSCRIPTION FACTOR APRF (ACUTE PHASE RESPONSE FACTOR)

FIELD OF THE INVENTION

The present invention is related to a novel transcription factor, acute phase response factor (abbreviated APRF hereafter), DNA's encoding it, evaluating and screening methods for searching an inhibitory agent against the function of APRF and an inhibitory agent against the function of the APRF.

More particularly, the present invention is related to APRF which is the transcription factor related to signal transmission of interleukin 6 (abbreviated as IL-6 hereafter) in cells, process for the preparation, DNA's encoding it, replication and expression vector comprising the DNA, host cells transformed or transfected with the replication and expression vector, evaluating and screening method for searching an inhibitory agent against the function of APRF and an inhibitory agent against the function of the APRF.

RELATED ARTS AND PROBLEMS

Bio-signal transmitter mediates the response of cells by transmitting signals stimulated by bioactive substance into cells. In a narrow sense, bio-signal transmitter means a substance which receives a signal from the receptor of a bioactive substance and regulates the expression of the gene in the nucleus. In the bio-signal transmitting substance, a protein which binds nucleus DNA and regulates the expression of the gene was called transcription factor or transcription factor. In this invention, these factors called transcription factors.

Generally, transcription factors per se are proteins. The transcription factor has a function of transmission of information (signal) to DNA in the nucleus from a primary bioactive mediator to cells, and has a function of regulating the expression of the second protein at the transcription stage. That is, transcription factor mediates in cells when the first bioactive substance acts to cells and the second protein will be expressed. Transcription by the said transcription factor includes to increase (accelerate) the expression and to decrease (restrain) the expression. The second protein regulated its expression by the act of the first protein will be called inducible protein and the gene corresponding to this protein will be called inducible gene in the present invention. For example, the protein induced by IL-6 such as haptoglobin, will be called IL-6 inducing protein and the gene of the said protein such as haptoglobin gene, will be called IL-6 inducible gene.

Example of the proteins promoted their expression by IL-6 are haptoglobin described above, hemopequisin, C-reactive protein, alpha2-macroglobulin, alpha1-acidic glycoprotein, and it is known that these proteins reveal remarkably in acute phase of inflammation. On the contrary, serum albumin is an example of protein suppressed their expression by IL-6.

Transcription substance binds a specific sequence of DNA of inducible gene and regulate the expression of the said inducible gene. Generally, DNA sequence which is bound by transcription factor exists near the promoter region, upstream of the inducible gene. DNA sequence which was bound by the transcription factor is inherent accordance with kinds of the transcription factor. The recent study of the transcription factor is described in Literature 1: Montminy, M., Science, 261, 1694 (1993).

Hitherto, NF-IL6 is known as transcription factor related to intracellular signal transmission of IL-6 (See Literature 2: Akira, S. et al., EMBO. J. 9, 1897 (1990), Literature 3: Poli, V. et al., Cell, 63, 643 (1990), Literature 4: Kinoshita, S. et al., Proc. Natl. Acad. Sci. U.S.A., 89, 1473 (1992) etc.).

However, there is no description about the transcription substance which transmits transcription signal to IL-6 inducible gene in nucleus directly from IL-6 receptor in the above literatures. On the other hand, it was known that the sequence: CTGGGA exists upstream of some IL-6 inducible gene. So, some substance which will be activated by IL-6 and bound the said sequence would be suggested in the literature 5: Wegenka, U. M. et al., Mol. Cell. Biol., 13, 276, 1993. But in the literature, existence of the said protein factor was suggested, but the sequence, structure, physical or chemical properties such as molecular weight of the said factor is not clarified. The substance transcription factor APRF per se is not disclosed in the literature.

Transcription substance exists in cells and ordinarily it regulates the transcription of inducible gene by being phosphorylated, moving into nucleus and binding to a proper DNA sequence, when bioactive substance (1st protein) binds to receptor of cells as described hereinbefore. So, substances which can affect the action of the said transcription substance e.g. inhibition, may be used a treating agent for diseases related to the bioactive substance said above.

From above viewpoint, the present inventors aimed IL-6 which is related to inflammatory diseases etc. The present inventors isolated and purified APRF and decided the partial amino acid sequence, cloned the said gene, decided total nucleotide sequence and deduced total amino acid sequence of APRF as transcription factor and obtained APRF per se for the first time as substance.

The present inventors continued the study and established the evaluating and searching method with using APRF for substance which is useful for the treatment of diseases induced by IL-6 such as inflammatory diseases, leukemia, cancer, osteoclasia induced by activated osteoclast, pulmonary hypertension etc. And the present inventors also have been accomplished to obtain the said inhibitor. The present invention is accomplished based on this knowledge.

Techniques for Solving the Problem

The present invention provides substantially purified mammalian transcription factor APRF.

Substantially purified form means, for example, in the case of the polypeptide shown in SEQ ID No:1 or 5, the polypeptide in a preparation in which more than 90%, e.g. 95%, 98% or 99% of the polypeptide in the preparation is that of the SEQ ID No:1 or 5.

APRF of the present invention described above have novel primary amino acid sequence. There was no polypeptide having amino acid sequence which is identical to that of the polypeptide of the present invention, when amino acid sequences of the polypeptide was compared by a computer to all known sequences in data base of Swiss Prot (Swiss Prot Release 2.0). Furthermore, there was no nucleotide sequence which is identical to that encoding the polypeptide of the present invention, when the DNA sequence was compared by a computer to all known sequences in data base of GenBank (GenBank Release 70.0).

The detailed description of APRF of the present invention are as follows: About APRF, isolation, purification, decision of the partial amino acid sequence, cloning of cDNA, decision of the sequence of the total amino acid etc. may be carried out by the embodiment method described hereafter. Summary of the method is as follows.

That is, mouse is administered IL-6 and killed 15 min. after administration. Nucleoprotein fraction is extracted from liver. The extract is purified with the column which was fixed DNA oligomer having the following sequence:

CCTTCCGGGAATTC (SEQ ID NO:10)

and purified with electrophoresis on polyacrylamide gel.

The purified product is hydrolyzed with lysyl endopeptidase. Digested products thus obtained are separated with high performance liquid chromatography and each peak is isolated. Amino acid sequence of peptide fragments obtained above are decided from N-terminal by automatic amino acid sequence analyzer.

Corresponding DNA oligomer is synthesized in accordance with the partial amino acid sequence decided above. cDNA of APRF is isolated from mammal cDNA library of liver or placenta with using the DNA oligomer. Amino acid sequence of APRF protein decided from the cDNA sequence of APRF.

In the present invention, examples of mammals are human, mouse, rat etc. APRF in which some amino acid sequence is replaced, lacked or inserted may be produced according to the producing tissue or cells although in the same species. The present invention also includes such subtype APRF.

The present invention includes human APRF as an embodiment. Polypeptide having amino acid sequence shown in SEQ ID No:1, homologue thereof, fragment thereof are included in the present invention concretely.

The present invention provides DNA encoding the above human APRF. The present invention also supplies DNAs having nucleotide sequence shown in SEQ ID No:2 and 3, DNA's which can be hybridizing to the said DNA's and fragments thereof.

Especially, according to the present invention, (1) a polypeptide having an amino acid sequence shown in SEQ ID No:1, (2) a DNA encoding the polypeptide described above (1), (3) a DNA having a nucleotide sequence shown in SEQ ID No:2, and (4) a DNA having a nucleotide sequence shown in SEQ ID No:3, provide as embodiments.

The present invention includes mouse APRF as an embodiment. Concretely, the present invention includes polypeptide having amino acid sequence shown in SEQ ID No:5, homologues thereof and fragments thereof.

Further, DNA encoding the said mouse APRF polypeptide is also provided according to the present invention. Concretely, DNAs having each nucleotide sequence shown in SEQ ID No:6 or 7, DNAs which can be hybridizing to the said nucleotide and fragment thereof will be provided.

Especially, according to the present invention, (5) peptide including amino acid sequence shown in SEQ ID No:5

(6) a DNA encoding the polypeptide described above (5)

(7) a DNA having a nucleotide sequence shown in SEQ ID No:6, and (8) a DNA having a nucleotide sequence shown in SEQ ID No:7 provide as embodiments.

In the present specification, polypeptides described in (1) and (5) having amino acid sequence shown in SEQ ID No:1 or 5 include not only polypeptides (natural mature protein) having amino acid sequence shown in SEQ ID No:1 or 5, but also for example, polypeptides which are added proper distinct amino acids or amino acid sequence less than 20% number of total amino acid shown in SEQ ID No:1 or 5, preferably less than 5% to N- or C-terminal, derivatives wherein amino acid(s) or amino acid sequence which is not related functionally are changed (deletion, replacement to other amino acid sequence, addition of other amino acid sequence, insertion etc.) including homologues and fragments thereof described hereafter, on the assumption that they possess equivalent biological and pharmacological properties.

A polypeptide homologue of the SEQ ID No:1 or 5 will be generally over a region of at least 100, preferably at least 150, for example 200, 250 or 300 continuous amino acids, at least 70%, preferably at least 80 or 90% and more preferably at least 95% homologous to the polypeptide shown in SEQ ID No:1 or 5. Such polypeptide homologues will be referred to below as a polypeptide according to the invention.

Further, fragments of the polypeptide of the present invention will be at least 10, preferably at least 15, for example 20, 25, 30, 40, 50 or 60 amino acids in length, and are also encompassed by the term "a polypeptide according to the invention" as used herein.

Polypeptides except for the polypeptide having amino acid sequences shown in SEQ ID No:1 or 5 and fragments thereof of the present invention have equivalent properties to the polypeptides having amino acid sequences shown in SEQ ID No:1 or 5, physiologically or pharmacologically. So, the present invention will provide not only the polypeptide having amino acid sequence shown in SEQ ID No:1 or 5, but also homologous polypeptides having equivalent properties physiologically or pharmacologically.

A DNA can be hybridized to the DNA's shown in the SEQ ID No:2, 3, 6 or 7 will be generally over a region of at least 100, preferably at least 150, for example 200, 250 or 300 continuous nucleotide sequence region, at least 70%, preferably at least 80 or 90% and more preferably at least 95% complementary to the DNA shown in SEQ ID No:2, 3, 6 or 7. Such DNA complements will be referred to below as a DNA according to the invention.

DNA fragments of the present invention means nucleotide part containing at least 10, preferably 15, for example 20, 25, 30 or 40 nucleotide of the DNA of the present invention, and such fragments are equivalent to the DNA of the present invention.

The DNA of the present invention, specified in (2) or (6) includes a group of every nucleotide sequences encoding polypeptides shown in SEQ ID No:1 or 5.

As known well, there are one to six kinds of codon as that encoding one amino acid (for example, one kind of codon for Methioine (Met), and six kinds of codon for leucine (Leu) are known).

As representative nucleotide sequence encoding amino acid sequence shown in SEQ ID No:1 or 5, nucleotide sequence shown in SEQ ID No:2, 3, 6 or 7 may be illustrated. DNAs of the present invention includes DNAs selected voluntary codon without changing amino acid sequence encoding. There is a probability of improving a yield of production of a polypeptide by changing a nucleotide sequence.

The DNA specified in (3) or (7) is the embodiment of DNA shown in (2) or (6), respectively and is sequence in the natural form.

The DNA shown in (4) and (8) indicates the sequence of the DNA specified in (3) or (7) with a non-translational region.

The DNA of the present invention (including fragments thereof, identical hereafter) may be prepared by known methods, for example, gene recombination, chemical synthesis etc. Details of the preparation are illustrated in the following examples. For example, DNA's having nucleotide sequences shown in SEQ ID Nos:3 and 7 may be prepared according to the following methods, that is:

(i) by isolating mRNA from cells which produce the polypeptide of the present invention, (ii) by preparing first strand (single stranded DNA) from mRNA thus obtained, followed by preparing second strand (double stranded DNA) (synthesis of cDNA), (iii) by inserting cDNA thus obtained into a proper plasmid vector, (iv) by transforming host cells with the recombinant DNA thus obtained (preparation of cDNA library), (v) by isolating plasmid containing desired DNA and cDNA library by hybridization method and (vi) by deciding desired nucleotide sequence.

Explained in detail, step (i) can be carried out in accordance with the method of Okayama, H. et al. (described in Methods in Enzymology, vol. 154, p 3, (1987)), or with the method of Chirgwin, J. M. et al. (described in Biochem., 18, 5294 (1979)) using mammalian, for example human or rat, tissue which is thought that APRF is expressed: Preferably, liver, macrophage, placenta tissue cells or cell line can be used.

Steps (ii), (iii) and (iv) are a series of steps for preparing cDNA library, and can be carried out in accordance with the method of Gubler & Hoffman (Gene, vol. 25, pp. 263, 1983) with a slight modification. As examples of the plasmid vector used in the step (iii), many vectors functioning in an *E. coli* strain (e.g., pBR 322) and in a *Bacillus subtilis* (e.g., pUB 110) are known, and λ-ZAPII etc. which functions in an *E. coli*, can be preferably used. In step (iv), any host cells can be used, and DH5 competent cell which has been prepared in accordance with the method described in Gene, 96, 23 (1990), can be preferable used. Recently, cDNA libraries of kinds tissues of animals can be available on the market. For example, cDNA library of mouse liver λ gt 11 and cDNA library of human placenta are on sale from Clontech. The said cDNA libraries on the market can be preferably used.

Step (v) can be carried out by known method per se, for example by plaque hybridization method, colony hybridization method (Gene, 10, 63 (1980)). DNA of APRF of other animals, homologues thereof, fragments thereof are illustrated as suitable probes.

Step (vi) is known per se, it can be carried out according to dideoxy terminator method or Maxam-Gilbert method.

Once the nucleotide sequences shown in SEQ ID Nos:2, 3, 6 and 7 are determined, DNA of the present invention can be obtained by chemical synthesis, by PCR method or by hybridization making use of a fragment of DNA of the present invention, as a probe. Furthermore, DNA of the present invention can be obtained in a desired amount by transforming with a vector DNA inserted a DNA of the present invention into a proper host, followed by culturing the transformant.

A further embodiment of the invention provides replication and expression vectors comprising DNA according to the invention. The vectors can be, for example, plasmid, virus or phage vectors provided with an origin of replication, optionally a promoter for the expression of the said DNA and optionally a regulator of the promoter. The vector may contain one or more selectable marker genes, for example a ampicillin resistance gene.

The present invention also provides host cells transformed or transfected with the vectors for the replication and expression of DNA according to the invention, including the DNA SEQ ID No:2, 3, 6 or 7 including the open reading frame thereof. Host cells using in the transformation can be cells of bacteria, yeast, insect or mammals. Transformation can be carried out by each method commonly used.

The polypeptide of the present invention (including fragments thereof, identical hereafter) can be expressed (produced) and accumulated using the said transformant cells which comprises culturing under conditions effective to express. Culturing conditions are well known in accordance with host cells used. Desired polypeptide produced and accumulated intracellular or extracellular of the said transformant cells can be isolated and purified by the common isolation method utilizing the physical, chemical and biological properties of the said polypeptide. Thus, the polypeptide of the present invention i.e. APRF can be prepared with industrial scale. So, the present invention also provides the preparation method of the polypeptide APRF by gene recombination.

The polypeptides of the present invention (e.g. shown in SEQ ID No:1 or 5) can be prepared by:

(1) isolating and purifying from cultured cells, (2) chemically synthesizing, or (3) gene recombination, preferably, by the method described in (3) for industry.

The preparation of the polypeptide of the present invention by gene recombination can be carried out more preferably, using the expression system (host-vector system) as follows.

For example, the expression in *E. coli* can be carried out by connecting the DNA encoding the protein (e.g. DNA having nucleotide sequence shown in SEQ ID No:2 or 6) to the downstream of a proper promoter (e.g., trp promoter, lac promoter, λ PL promoter, T7 promoter etc.), and then inserting it into a vector (e.g., pBR322, pUC18, pUC19 etc.) which functions in an *E. coli* strain to prepare an expression vector.

Then, an *E. coli* strain (e.g., *E. coli* DH1 strain, *E. coli* JM109 strain, *E. coli* HB101 strain, etc.) which is transformed with the expression vector thus obtained can be cultured in a proper medium to obtain the desired polypeptide. When a signal peptide of bacteria (e.g., signal peptide of pel B) is utilized, the desired polypeptide can be also produced in periplasm. Furthermore, a fusion protein with other polypeptide can be also produced easily.

Furthermore, the expression in a mammalian cell can be carried out, for example, by inserting the DNA shown in SEQ ID No:3 or 7 into the downstream of a proper promoter (e.g., SV40 promoter, LTR promoter, metallothionein promoter etc.) in a proper vector (e.g., retrovirus vector, papilloma virus vector, vaccinia virus vector, SV40 vector, etc.) to obtain an expression vector, and transforming a proper mammalian cell (e.g., monkey COS-7 cell, Chinese hamster CHO cell, mouse L cell etc.) with the expression vector thus obtained, and then culturing the transformant in a proper medium to get a desired polypeptide in the culture medium.

As is said above, the polypeptide of the present invention i.e. transcription factor APRF have a function to regulated the transcription related to the intracellular signal transmission by binding a specific DNA part of IL-6 inducible gene in nucleus. So, APRF is useful, for example, for the clarification the diseases induced by the action of IL-6, for the study or development of the said inhibitor for the treatment of the said diseases.

By using the present invention, it can be carried out to search and evaluate an inhibiting substance on the function of APRF. The present invention also provides the screening method for searching inhibiting substance on the function of APRF.

The function of APRF includes being phosphorylated of itself, transition into nucleus, binding to DNA. The said inhibition means inhibition on at least one of the above function of APRF. The present inventors found out that APRF exists in a certain cells, and be activated by phosphorylation when IL-6 acts to the cells. It was known that transcription factor will transit into nucleus and bind to specific DNA sequence, when the factor is phosphorylated. So, the inhibition can be achieved by inhibition on the stage of phosphorylation, on the transition to nucleus or on the expression stage of APRF itself etc.

Further, the present invention also provides an agent containing an inhibitor of the function of APRF, as active ingredient.

The above active ingredient includes, for example, polypeptide having amino acid sequence containing SEQ ID No:1 or 5, homologues thereof, fragments thereof, antibody obtained from mammals which was immunized homologue or fragment of the said polypeptide, nucleic acid or derivatives thereof which can bind APRF, antisense nucleic acid of APRF gene, expression vector containing antisense nucleic acid, ribozyme which can decompose mRNA of APRF.

APRF antibody which inhibits the function of APRF can be easily prepared in conventional manner, for example, by synthesizing peptide as a proper immunogen in accordance with the amino acid sequence of APRF or the present invention immunizing an animal by administration the peptide.

The antibody obtained above is useful for an inhibitor of the function of APRF and also is important to know behavior of APRF per se in cells or living body. It can be designed lower molecular APRF inhibitor accordance with the recognition pan of the said antibody. The present invention includes the said lower molecular APRF inhibitor.

For suppression of the function of APRF, antisense nucleic acid of APRF genes per se or a proper expression vector transfected with the said antisense nucleic acid would be administered to cells or living body. The said antisense nucleic acid or expression vector containing the said antisense can be used as an active ingredient for the inhibitor of the function of APRF of the present invention.

Further, ribozyme which can decompose the mRNA of APRF of the present invention also inhibits the function of APRF, so the ribozyme also can be used as active ingredient of the inhibitor of the function of APRF.

APRF protein or derivative thereof which is partially-modified by gene recombination can be used for complementation or suppression of the function of APRF in cells or living body. The same purpose can be achieved by administration of APRF gene or derivative gene thereof which was partially-modified by gene recombination into cells or living body.

The present invention also provides inhibiting agent containing the. inhibitor on the function of APRF of the present invention. The said inhibiting agent may be administered by a proper formulation (administration form) which can be exerted its action in cells or living body. For example, the agent may be prepared as liposome etc. which is modified proper modification on its surface to design the active ingredient can be taken in nucleus directly and it may be administered from proper route accordance with the formulation.

New treating method for diseases induced by IL-6 will be found by using the inhibitor of the present invention.

APRF is newly isolated and assigned by the present inventors as a protein related to intracellular signal transmission of IL-6. On the other hand, in some case, a certain transcription factor also relates transmission of the signals of other bioactive substance. So, the inhibition of APRF may be useful for not only diseases induced by IL-6, but also for diseases induced by other bioactive substance wherein APRF mediates the signal transmission. The present inventors have been found out independently that phosphorylation of APRF is induced by other cytokines other than IL-6, for example, by oncostatin M, leukemia inhibitory factor, interleukin 11, ciliary neurotrophic factor etc. really. The inhibitory agent on the function of APRF, of the present invention also be useful for treatment of diseases induced by the said cytokines.

EXAMPLES

The following examples are illustrated in detail and concretely, but not limit, the present invention.

Example 1

Isolation of APRF

APRF was isolated from nucleus extract of livers of mice which were administered human IL-6 and killed 15 min. after administration.

(1) Isolation of nuclear extract

Nuclear extract was prepared by the method of Wegenka, U. M. et al (Mol. Cell. Biol., 13, 276(1993)) with minor modifications.

Mice were administered intravenously human IL-6 (5 µg/mouse), and killed 15 min. after administration. Mice livers were immediately immunized into ice-cold HANKS solution containing 1 mM orthovanadate. Then the livers were homogenized in homogenization buffer containing 10 mM HEPES (pH 7.6), 0.5 mM spermidine, 0.15 mM spermine, 25 mM KCl, 1 mM EDTA, 1 mM EGTA, 1 mM dithiothreitol (DTT), 1 mM phenylmethylsulfonyl fluoride (PMSF), 10% glycerol with 0.3M sucrose (3 ml per one liver) by 20 strokes in a motor-driven Teflon-glass homogenizer on ice.

Aprotinin (10 µg/ml), leupeptin (2 µg/ml), pepstatin (2 µg/ml), and 1 mM orthovanadate were added prior to homogenization. Nuclei were isolated by centrifugation laying homogenization buffer containing 2M sucrose under the homogenate at 27,000 rpm in an SW28 rotor (Hitachi) for 30 min. at 4° C.

After the supernatant was removed, the nuclei from 10 livers were resuspended in 1 mM of nuclear extraction buffer (50 mM Tris (pH 7.8), 420 mM KCl, 5 mM MgCl2, 0.1 mM EDTA, 2 mM DTT, 0.5 mM PMSF) with protease inhibitors and phosphatase inhibitors. After gentle agitation for 30 min. at 4° C., the mixture was centrifuged at 27,000 rpm in SW28 rotor for 30 min., then the supernatant was subjected to dialysis against dialysis buffer (20 mM HEPES (pH 7.8), 50 mM KCl, 12.5 mM MgCl2, 1 mM EDTA, 1 mM DTT, 1 mM PMSF, 0.1% Nonidet P-40 (BDH Laboratory), 20% glycerol) with protease inhibitors and phosphatase inhibitors. The extract was centrifuged against to remove insoluble precipitates.

(2) Isolation of APRF

The nuclear extracts (from 3000 livers of mice) prepared in (1) were incubated for 30 min. at 4° C., with streptavidin-conjugated paramagnetic beads (Dynabeads M-280 streptavidin, Dynal) containing high-affinity APRF binding site oligonuleotides (5-biothinylatd tandem palindromic APRF consensus sequence, 2×CCTTCCGGGAATTC, SEQ ID No:10) in the presence of salmon sperm DNA (200 µg/ml).

Binding proteins were extensively washed with washing solution (20 mM HEPES (pH 7.9), 1 mM EDTA, 5 mM MgCl2, 0.05% NP-40, 10% glycerol) and eluted with washing solution containing 1 M KCl. Elutes were immediately diluted with washing solution and again incubated with the magnetic beads with APRF binding sites.

After three rounds of DNA affinity chromatography the elute was separated by SDS-PAGE. Purified product contains 95 kd polypeptide (main band), 85 kd and 70 kd polypeptide (sub band). All the proteins was phosphorylated at tyrosine residue. The proteins were not detected from the extract of cells which were not treated IL-6.

A 95 kd phosphoprotein band was eluted from the gel, precipitated with 10% (v/v) trichloroacetic acid, washed with acetone, and dissolved in a buffer containing 8M urea and 10 mM Tris, pH 9.0. The protein was digested with lysyl endopeptidase for 6 hr. at 37° C. The resulting peptides were separated by reverse-phase high pressure liquid chromatography using a 0.1% (v/v) trifluoroacetic acid and acetonitrile gradient on a 1 mm×25 cm RP-300 column (Applied Biosystems).

The resolved peptides were collected and sequenced by automated Edman degradation on a Applied Biosystems Model 477A sequencer. Amino acid sequence of the peptide was clarified. The fragment was called peptide 3 hereafter.

Thr Gln Ile Gln Ser Val Glu
Pro Tyr          (SEQ ID No:1, residues 632–640)

Example 2 cDNA cloning of APRF

An aliquot of phage template DNA from a mouse liver λ gt 11 cDNA library (CLML 1035b; Clontech) was amplified by PCR with a degenerate oligonucleotide:

5'-AC(AGCT)CA(AG)AT(ACT)-
CA(AG)TC(AGCT)GT-3'          (SEQ ID No:11)

from peptide 3 and a λ gt 11 vector reverse primer, and PCR product with a unique DNA sequence which encoded the extract amino acid sequence of peptide 3 was obtained. PCR was carried out for 30 cycles, for 1 min. at 94° C., for 1 min. at 55° C. and for 2 min. at 72° C. as one cycle.

It was confirmed that PCR product having correct amino acid sequence peptide 3 was obtained from the result of subcloning cDNA amplified above into pT7 Blue T vector (Novagen).

Approximately 1.5×10 6 plaques of mouse liver and macrophage λ gt 11 cDNA libraries (alienated from Dr. Shigekazu Nagata of Osaka Bioscience Laboratory), respectively were screened by plaque hybridization using the PCR product as probe.

Hybridization was carried out in 6× SSC adding 5× Denhardt's solution (0.1% Ficoll, 0.1% polyvinylpyrrolidone and 0.1% bovine serum albumin) and 0.5% SDS (sodium dodecyl sulfate), at 65° C. for 15 hr. The filter was washed twice with 2× SSD containing 1% SDS at 65° C. for 30 min.

Positive clones were isolated and sequencing analyzed. Nucleotide sequence of cDNA was analyzed by a dideoxy chain termination method with double strand.

The said positive clone was analyzed as total length cDNA clone of mouse APRF having open reading frame of 2310 bp (shown in SEQ ID No:6).

The said total nucleotide sequence is shown in SEQ ID No:7. Amino acid sequence deduced from open reading frame is shown in SEQ ID No:5.

cDNA of human APRF was isolated using the same probe and the same conditions, by screening a human placental cDNA library (CLHL 1008b; Clontech).

Total length nucleotide sequence and open reading frame nucleotide sequence are shown in SEQ ID Nos:3 and 2, respectively. Amino acid sequence deduced from open reading frame is shown in SEQ ID No:1.

Example 3

Northern blotting analyses

Total RNA was prepared from mouse tissues by cesium chloride gradiation method. Poly(A)+ RNA was purified with Oligo-dT Latex (Oligotex-dT30, Roche). Three µg of poly(A)+ RNA was subjected to agarose gel electrophoresis then the RNA was transferred to a nylon membrane (Hybond Plus; Amersham). For human tissues, an RNA blotted membrane (Human Multiple Tissue Northern Blot) was purchased from Clontech.

The membrane was hybridized with a radio labeled DNA probe containing from nucleotide 806 to 1200 of mouse APRF for mouse sample, and 238–726 of human APRF for human samples. The membrane were washed, then dried and autoradiographed. For internal control, the membranes were rehybridized with the actin probe.

---

What is claimed:

1. An isolated DNA molecule which encodes a human APRF polypeptide having the amino acid sequence of SEQ ID No:1.

2. An isolated DNA molecule comprising the nucleotide sequence of SEQ ID NO:2.

3. An isolated DNA molecule comprising the nucleotide sequence of SEQ ID NO:3.

4. A replication or expression vector comprising the DNA molecule of claim 1, 2 or 3.

5. A host cell transformed or transfected in vitro with the replication or expression vector of claim 4.

6. A method of producing mammalian acute phase response factor (APRF) having the amino acid sequence of SEQ ID NO:1 comprising culturing a host cell transformed or transfected with the replication or expression vector of claim 4.

7. The host cell of claim 5 which is an *Escherichia coli*, a COS cell, a CHO cell or a mouse L cell.

8. The method of claim 6, wherein said host cell is an *Escherichia coli*, a COS cell, a CHO cell or mouse L cell.

* * * * *